United States Patent [19]

Pawelka et al.

[11] Patent Number: 5,505,704
[45] Date of Patent: Apr. 9, 1996

[54] MANIFOLD MEDICATION INJECTION APPARATUS AND METHOD

[75] Inventors: Gerhard E. F. Pawelka, Lexington, Mass.; Christopher J. Stringer, San Francisco, Calif.; Matthew Marsh, San Francisco, Calif.; David L. Karshmer, San Francisco, Calif.; Christopher O. Lada, Palo Alto, Calif.; Stephen J. Schoenberg, Redwood City, Calif.

[73] Assignee: Eli Lilly and Company, Indianapolis, Ind.

[21] Appl. No.: 458,013

[22] Filed: Jun. 1, 1995

Related U.S. Application Data

[63] Continuation of Ser. No. 335,674, Nov. 8, 1994, abandoned, which is a continuation of Ser. No. 41,758, Apr. 2, 1993, abandoned.

[51] Int. Cl.⁶ ..................................................... A61M 3/00
[52] U.S. Cl. ................. 604/191; 604/82; 604/51
[58] Field of Search ............................. 604/82, 191, 187, 604/207, 208–211, 186, 218, 228, 236, 232–233, 235

[56] References Cited

U.S. PATENT DOCUMENTS

| | | |
|---|---|---|
| 1,093,471 | 4/1914 | Porter . |
| 2,112,160 | 3/1938 | Johnson ................... 604/82 |
| 2,221,739 | 11/1940 | Reiter . |
| 2,632,445 | 3/1953 | Kas, Sr. . |
| 3,002,517 | 10/1961 | Pitton . |
| 3,110,310 | 11/1963 | Cislak . |
| 3,232,117 | 2/1966 | Gilmont . |
| 3,481,510 | 12/1969 | Allen, Jr. . |
| 3,517,668 | 6/1970 | Brickson . |
| 3,583,399 | 6/1971 | Ritsky . |
| 3,613,952 | 10/1971 | Gilmont . |
| 3,815,785 | 6/1974 | Gilmont . |
| 3,977,574 | 8/1976 | Thomas . |
| 4,018,223 | 4/1977 | Ethington . |
| 4,040,420 | 8/1977 | Speer ........................... 604/82 |
| 4,044,757 | 8/1977 | McWhorter et al. ........... 604/82 |
| 4,096,751 | 6/1978 | Withers . |
| 4,099,548 | 7/1978 | Sturm . |
| 4,275,729 | 6/1981 | Silver . |
| 4,333,458 | 6/1982 | Margulies . |
| 4,359,049 | 11/1982 | Redl et al. ..................... 604/82 |

(List continued on next page.)

FOREIGN PATENT DOCUMENTS

| | | | |
|---|---|---|---|
| 2074565 | 1/1993 | Canada | A61M 5/178 |
| 2108691 | 8/1993 | Canada | A61M 5/315 |
| 0058536A1 | 2/1982 | European Pat. Off. . | |
| 0268191 | 11/1987 | European Pat. Off. | A61M 5/28 |
| 0498737A1 | 2/1992 | European Pat. Off. | A61M 5/315 |
| 0627229A1 | 5/1994 | European Pat. Off. | A61M 5/315 |
| 1070784 | 12/1959 | Germany . | |
| 3840000A1 | 7/1989 | Germany | A61M 5/315 |
| 3903315A1 | 8/1989 | Germany | A61M 5/18 |
| 1198214 | 7/1970 | United Kingdom | A61M 5/22 |
| 2172937 | 10/1986 | United Kingdom | A61M 5/315 |
| WO92/10425 | 6/1992 | WIPO | A61M 5/18M |
| WO92/18179 | 10/1992 | WIPO | A61M 5/315 |
| WO93/10838 | 6/1993 | WIPO | A61M 5/20 |
| WO94/11039 | 5/1994 | WIPO | A61M 5/00 |
| WO94/15120 | 7/1994 | WIPO | F16H 31/00 |

Primary Examiner—C. Fred Rosenbaum
Assistant Examiner—Perry E. Van Over
Attorney, Agent, or Firm—Baker & Daniels

[57] ABSTRACT

A hand-held dual liquid medication injector have dual, bi-directional dosage metering mechanisms for permitting a variable dosage amount for each cartridge of liquid medication. The medications are mixed within a manifold having a valved mixing chamber and are injected via a single cannula. The mixing chamber is valved such that backflow of mixed or unmixed medications into the cartridges is prevented. An injection mechanism, independent of the metering mechanism, loads and injects the liquid medication. In one embodiment, downward movement of the injection mechanism during injection is translated into horizontal movement by the plunger mechanism. In another embodiment, a power-assisted plunger mechanism accomplishes injection.

55 Claims, 26 Drawing Sheets

U.S. PATENT DOCUMENTS

| | | |
|---|---|---|
| 4,367,739 | 1/1983 | LeVeen . |
| 4,381,778 | 5/1983 | Kozam et al. ............................ 604/191 |
| 4,395,921 | 8/1983 | Oppenlander . |
| 4,413,760 | 11/1983 | Paton . |
| 4,425,121 | 1/1984 | Young et al. . |
| 4,444,560 | 4/1984 | Jacklich . |
| 4,475,905 | 10/1984 | Himmelstrup . |
| 4,498,904 | 2/1985 | Turner . |
| 4,581,022 | 4/1986 | Leonard . |
| 4,592,745 | 6/1986 | Rex et al. . |
| 4,609,371 | 9/1986 | Pizzino . |
| 4,610,666 | 9/1986 | Pizzino ....................................... 604/91 |
| 4,631,055 | 12/1986 | Redl et al. ................................ 604/82 |
| 4,643,723 | 2/1987 | Smit . |
| 4,659,327 | 4/1987 | Bennett . |
| 4,664,128 | 5/1987 | Lee . |
| 4,673,395 | 6/1987 | Phillips . |
| 4,689,042 | 8/1987 | Sarnoff . |
| 4,710,172 | 12/1987 | Jacklich . |
| 4,710,178 | 12/1987 | Leonard et al. . |
| 4,755,169 | 7/1988 | Sarnoff . |
| 4,820,287 | 4/1989 | Leonard . |
| 4,874,368 | 10/1989 | Miller et al. .............................. 604/82 |
| 4,883,472 | 11/1989 | Michel . |
| 4,968,299 | 11/1990 | Ahlstrand . |
| 4,973,318 | 11/1990 | Holm . |
| 4,978,336 | 12/1990 | Capozzi et al. ........................... 604/82 |
| 5,104,375 | 4/1992 | Wolf et al. ................................ 604/82 |
| 5,104,380 | 4/1992 | Holman . |
| 5,112,317 | 5/1992 | Michelf . |
| 5,114,406 | 5/1992 | Gabriel . |
| 5,116,315 | 5/1992 | Capozzi et al. ........................... 604/82 |
| 5,135,507 | 8/1992 | Haber . |
| 5,147,323 | 9/1992 | Haber . |
| 5,226,895 | 7/1993 | Harris ...................................... 604/208 |
| 5,240,146 | 8/1993 | Smedley et al. .......................... 604/82 |
| 5,253,785 | 10/1993 | Haber . |
| 5,271,527 | 12/1993 | Haber . |
| 5,279,585 | 1/1994 | Balkwill . |
| 5,279,586 | 1/1994 | Balkwill . |
| 5,304,152 | 4/1994 | Sams . |
| 5,314,412 | 5/1994 | Rex . |

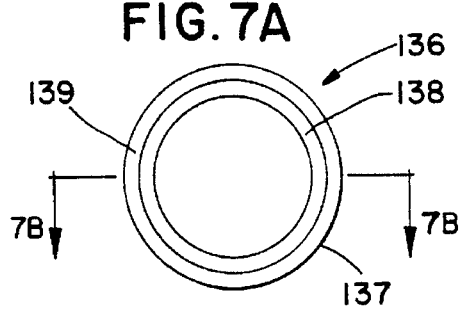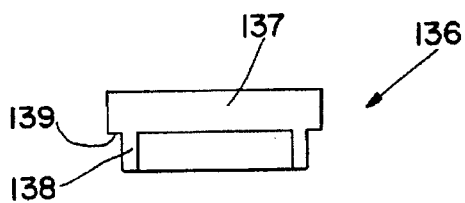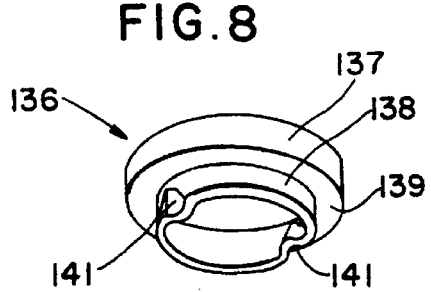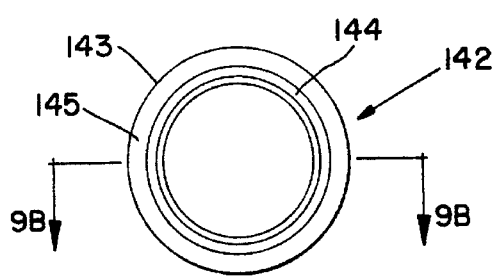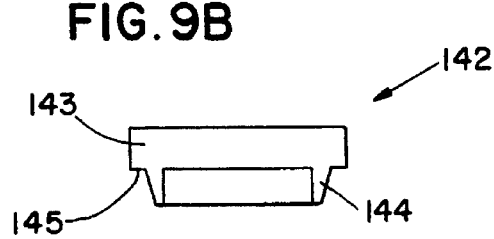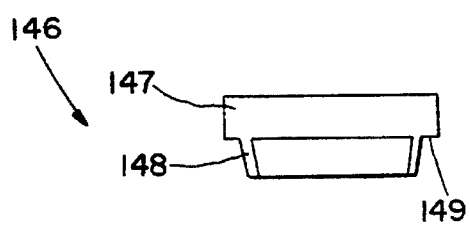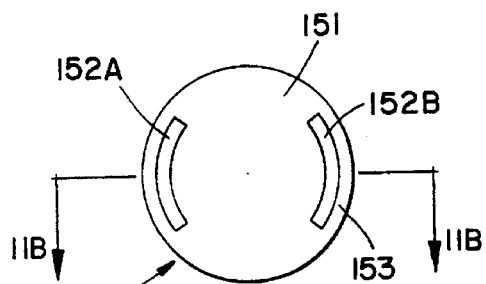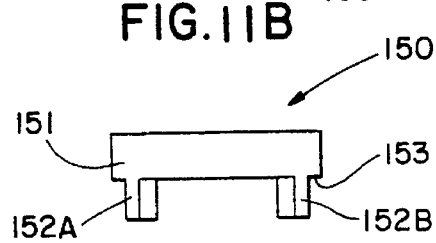

FIG. 21
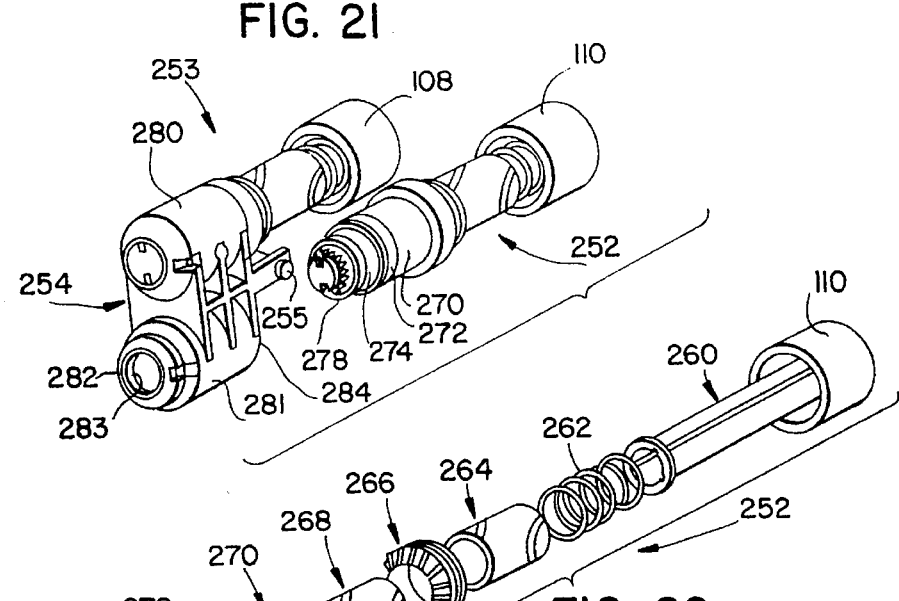
FIG. 22
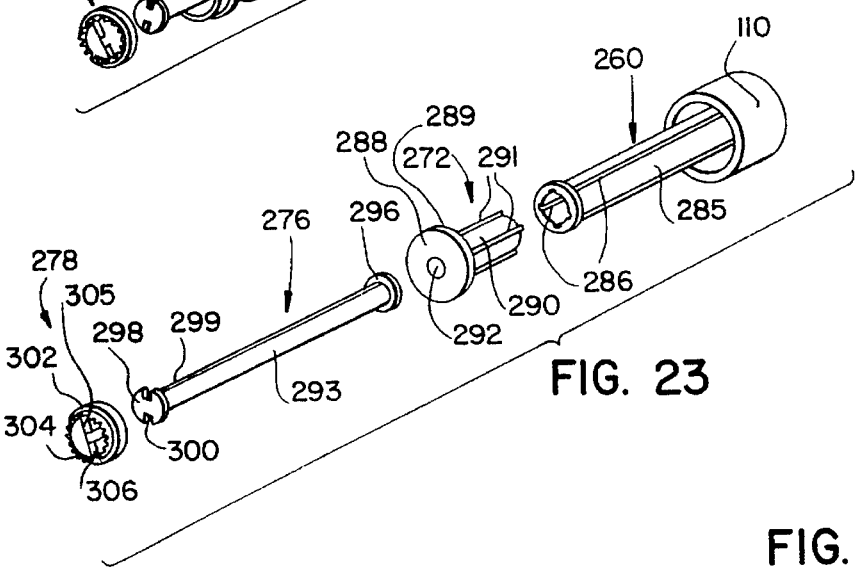
FIG. 23
FIG. 24
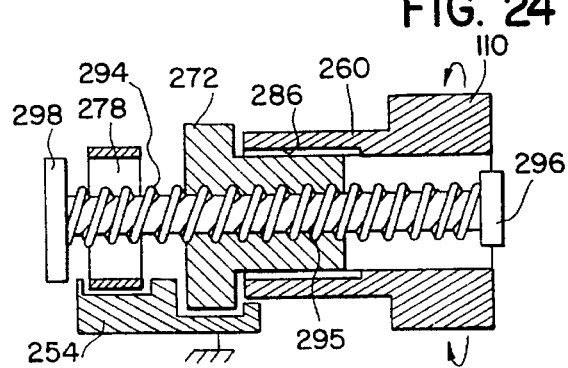

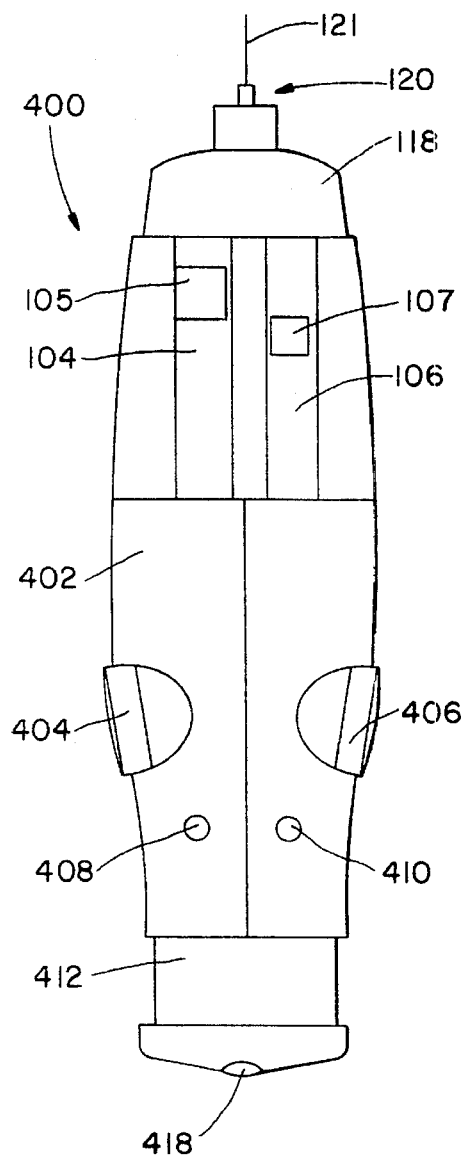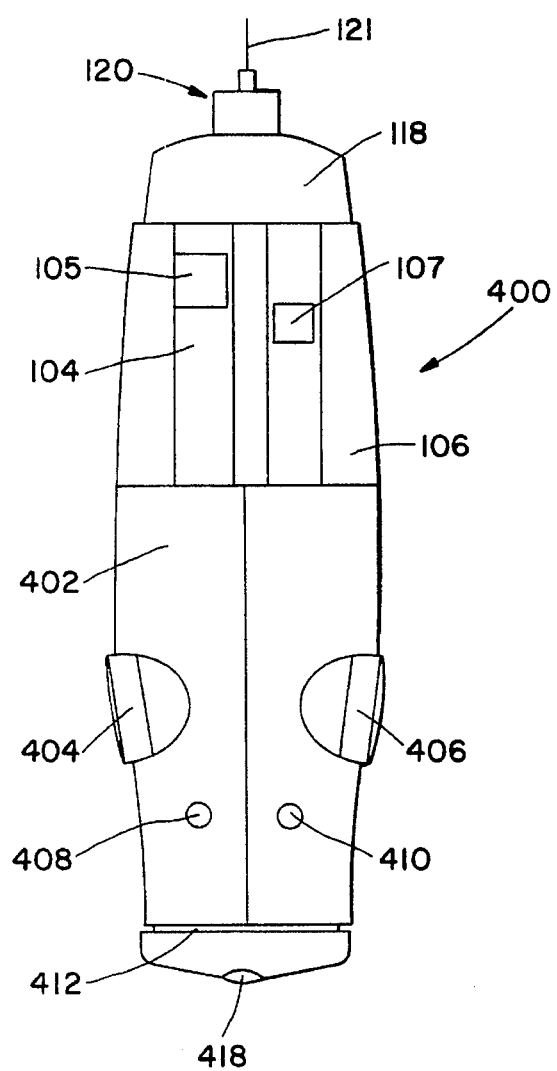

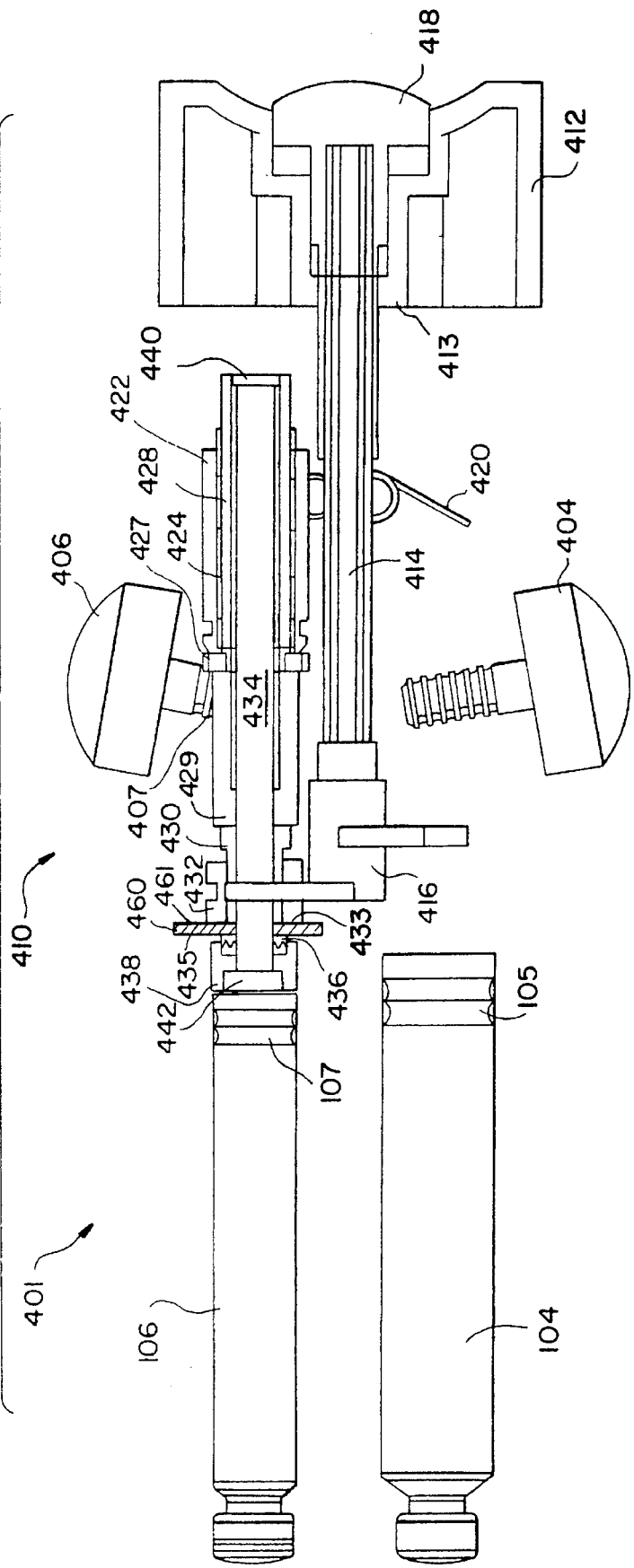

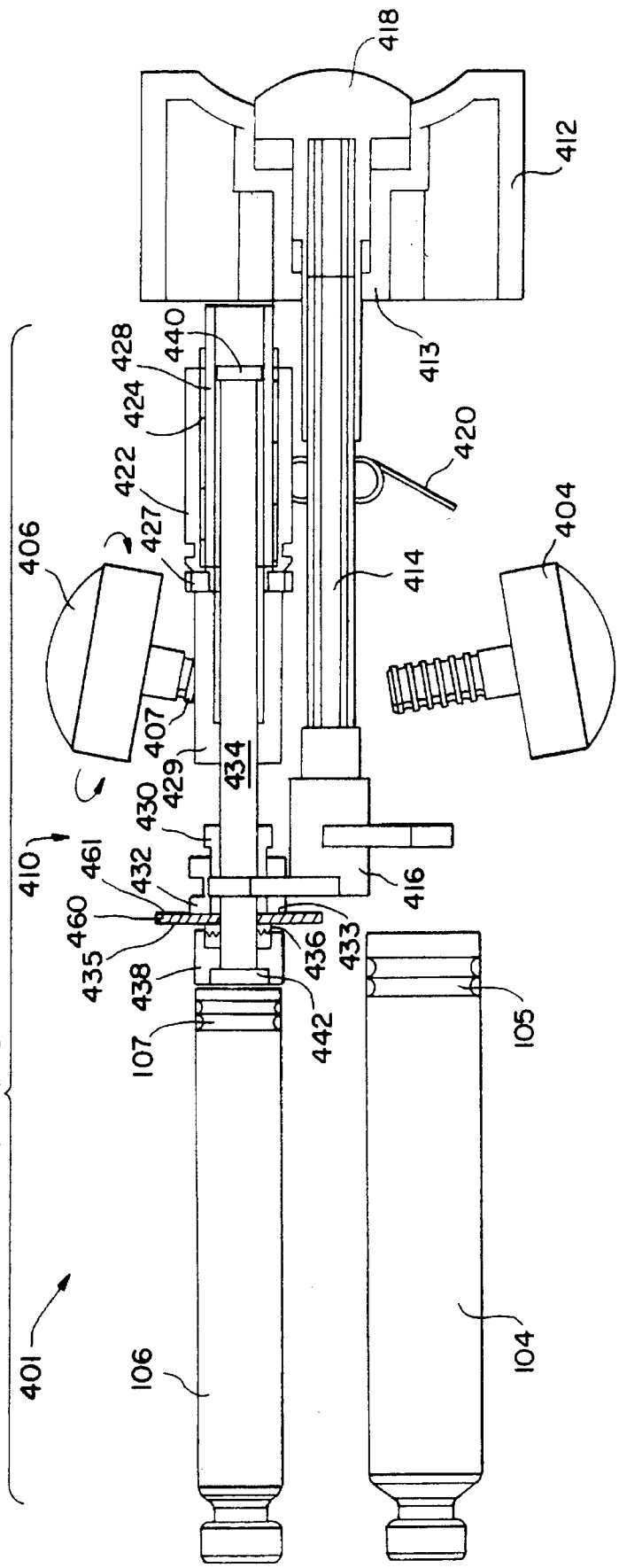

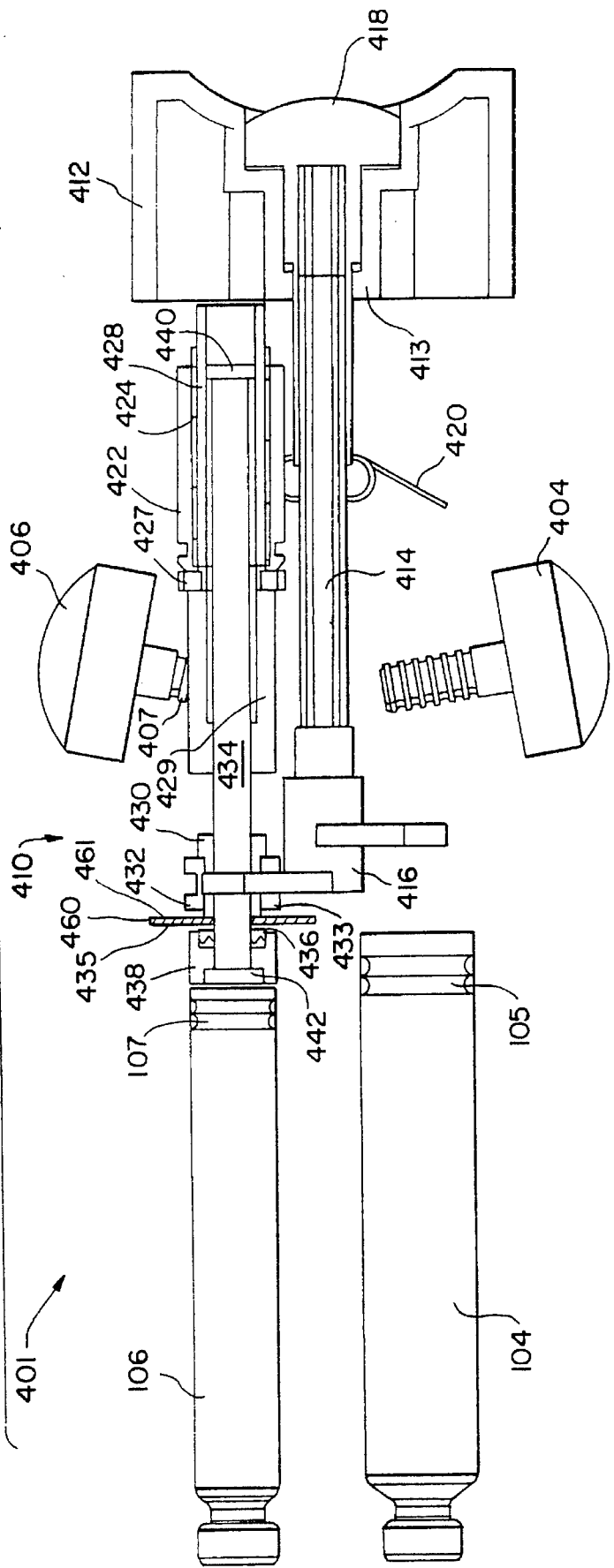

MANIFOLD MEDICATION INJECTION APPARATUS AND METHOD

This is a continuation of application Ser. No. 08/335,674, filed Nov. 8, 1994 now abandoned, which is a continuation of application Ser. No. 08/041,758, filed Apr. 2, 1993 now abandoned.

BACKGROUND OF THE INVENTION

The present invention relates to devices for injecting medication and, more particularly, to devices for injecting two or more medications simultaneously.

Injection devices are known that hold two cartridges of medication. The medication is forced to flow from the cartridges, through a manifold and out a single cannula in fluid communication with the manifold. Injection of the medications is accomplished by inserting the cannula into the patient and causing the medications to be expelled therefrom.

It is medically desirable in the treatment of certain conditions of the human body to administer several types and dosage amounts of medication simultaneously. The treatment of diabetes is one such example. Different types of insulin act in different fashions. A fast acting insulin, such as for example a regular insulin, works quickly but for a short period of time after administration. A longer acting insulin, such as for example an isophane insulin, takes effect more slowly but for a longer period of time. It is therefore medically desirable to simultaneously inject both regular and isophane insulin when needed. In order to most accurately simulate the natural glucose curve of the body, the insulin user would need to inject different ratios or combinations of regular and isophane insulin at different times of the day.

One prior art technique of simultaneous injection of regular and isophane insulin is termed premixing. A syringe is loaded from separate vials of regular and isophane insulin by measuring and dispensing the insulin in a time-consuming and tedious process.

Also, the same is accomplished by preestablished mixtures of regular and isophane insulin that are packaged in a single vial or cartridge. The insulin user however, is constrained to use the preestablished mixtures and can not customize the ratios. The simulation of the natural glucose curve of the human body may require four injections per day. Each injection would require a different ratio of regular to isophane insulin.

The injection of a liquid medicine requires an amount of force necessary to overcome the static load on the plunger within the medication cartridge as well as the dynamic pressure as the liquid medication is forced to exit from a restricted opening. As the plunger moves, a continuous force is necessary to keep the plunger moving such that the desired dosage amount is ejected from the cartridge.

SUMMARY OF THE INVENTION

The present invention provides a hand-held dual liquid medication injector have dual, bi-directional dosage metering mechanisms for permitting a variable dosage amount for each cartridge of liquid medication. The medications are mixed within a manifold having a valved mixing chamber and are injected via a single cannula. The valved mixing chamber preventing backflow of mixed or unmixed insulin into either cartridge. An injection mechanism, independent of the metering mechanism, loads and injects the liquid medication.

In one form thereof, the present invention provides an apparatus for injecting a medication into the body. The apparatus comprises a housing, a cartridge containing the medication and disposed within the housing, the cartridge defining an axis of ejection of the medication from the cartridge. Plunger means for ejecting the medication from the cartridge is included, the plunger means acting along the axis of ejection, as well as injection means for actuating the plunger means and causing injection of the medication into the body, the injection means including a hand operated actuating lever movable in a direction transverse to the axis of injection. The metering means permits bi-directional metering of the dosage amount.

In another form, the present invention provides a device for the simultaneous injection of two medications through a single cannula, the device comprising a housing, a first and second cartridge disposed within the housing, the first and second cartridges each containing a liquid medication. First means for metering a dosage amount of medication to be ejected from the first cartridge and second means for metering a dosage amount of medication to be ejected from the second cartridge is included. The injection device further includes means for simultaneously injecting the first and second metered amounts through the single cannula, the first and second metering means permitting bi-directional dosage metering of the respective medications. The injection means operates independently of the first and second metering means.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein:

FIG. 7A is a plan view of the flapper valve of FIG. 5;

FIG. 7B is a sectional view taken along line 7B—7B of FIG. 7A;

FIG. 8 is a perspective view of the flapper valve of FIG. 5 in a deformed condition to allow fluid flow thereby;

FIG. 9A is a plan view of an alternative embodiment of a flapper valve;

FIG. 9B is a sectional view of the flapper valve of FIG. 9A taken along line 9B—9B thereof;

FIG. 10A is a plan view of an alternative embodiment of a flapper valve;

FIG. 10B is a sectional view of the flapper valve of FIG. 10A taken along line 10B—10B thereof;

FIG. 11A is a plan view of an alternative embodiment of a flapper valve;

FIG. 11B is a sectional, view of the flapper valve of FIG. 11A taken along line 11B—11B thereof;

FIG. 21 is a partial exploded perspective view of the metering and shuttle assembly of FIG. 19;

FIG. 22 is an exploded perspective view of the metering mechanism of FIG. 19;

FIG. 23 is an exploded perspective view of a portion of the metering mechanism of FIG. 22;

FIG. 24 is an enlarged sectional view of the portion of the metering mechanism shown in FIG. 23;

FIG. 40 is an elevational view of the plunger-type dual medication injector apparatus according to one embodiment of the present invention;

FIG. 41 is an elevational view of the plunger-type dual medication injector apparatus of FIG. 1 with the plunger depressed during injection;

FIG. 56 is a partial sectional view of the injector device of FIG. 40 in a Steady state;

FIG. 57 is a partial sectional view of the injector device of FIG. 40 in a Metering state;

FIG. 58 is a partial sectional view of the injector device of FIG. 40 in a Brake Release/Inject state;

Corresponding reference characters indicate corresponding parts throughout the several views. The exemplification set out herein illustrates one preferred embodiment of the invention, in one form, and such exemplification is not to be construed as limiting the scope of the invention in any manner.

DETAILED DESCRIPTION OF THE INVENTION

Figure 1:
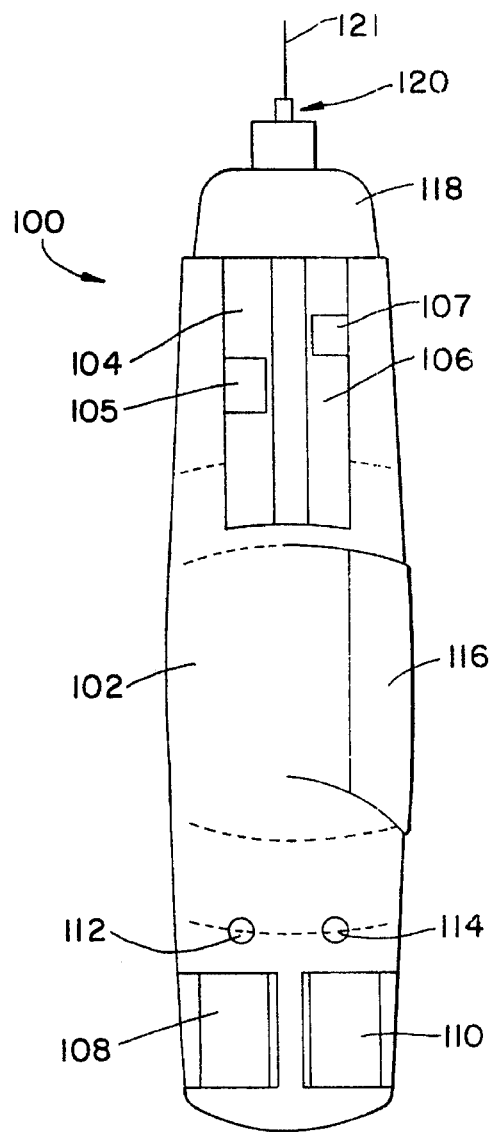
FIG. 1 is an elevational view of the wing-type dual medication injector apparatus according to one embodiment of the present invention.
Figure 2:
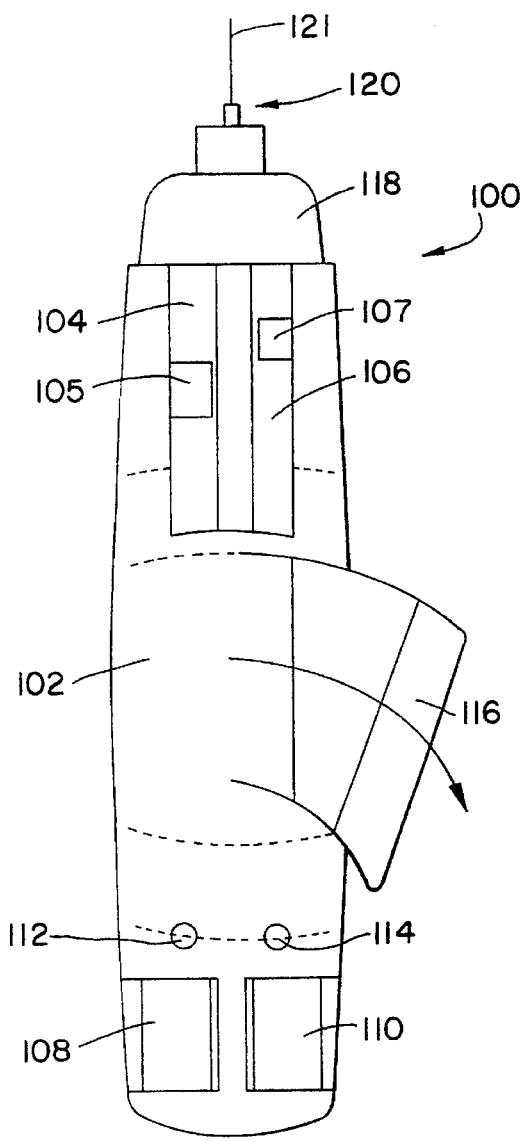
FIG. 2 is an elevational view of the wing-type dual medication injector apparatus of FIG. 1 with the wing cocked, ready for injection.

Referring to FIG.1 there is shown an embodiment of the present dual medication manifold injection apparatus 100 designated as the "wing-type." Injector 100 includes an elongated main body or housing 102 preferably of a plastic material. At one end of body 102 there are supported two conventional glass cartridges or vials 104, 106 of different injectable product or medication such as for example, insulin, each having a respective plunger 105, 107 disposed therein and rubber (disk) seals 245 (FIG. 18) on the ends thereof. Cartridge 104 is a 3.0 ml cartridge, while cartridge 106 is a 1.5 ml cartridge, for example, each being typical cartridge size of regular and isophane insulin in the industry, or insulin analogs, or any mixture of insulins. At the end of body 102 distal cartridges 104, 106 are two bi-directional metering knobs or dosage adjusters 108, 110 for dialing in or setting the desired dosage to be dispensed from respective cartridges 104, 106 during injection. Dose indicators 112, 114, located adjacent respective metering knobs 108, 110, display the dosage amount set via the respective metering knobs 108, 110. On one side of body 102 is a wing or lever mechanism or actuator 116. Wing 116, described in detail hereinbelow in connection with the operation of the present invention, is utilized to inject and reset the injection mechanism. FIG. 2 shows wing 116 in a cocked or loading position ready for the user to inject both medications from cartridges 104, 106. Wing 116, as depicted in FIG. 2, pivots or swings outwardly and inwardly from the side thereof.

Figure 3:
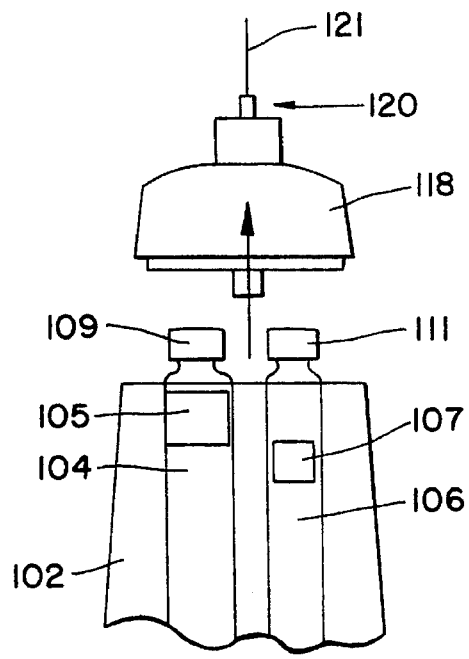
FIG. 3 is an exploded fragmentary view of the wing-type injector apparatus of FIG. 1 with the manifold cap removed.
Figure 4:
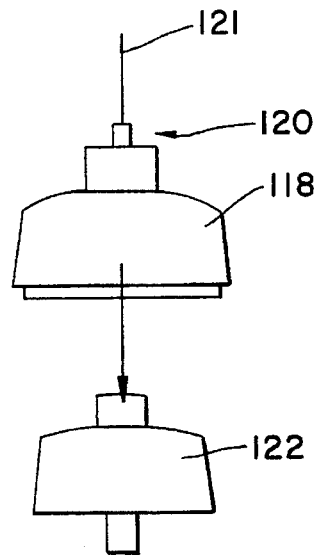
FIG. 4 is an exploded view of the manifold cap and removable manifold.

A plastic manifold cap 118 with a patient needle assembly 120 is disposed on the end proximate cartridges 104, 106. Referring to FIG. 3, manifold cap 118 fits over cartridge necks 109, 111 of respective cartridges 104, 106 and serves to properly seat and house a manifold assembly 122. As seen in FIG. 4, manifold assembly 122 is received within manifold cap 118 and functionally provides a fluid communication path between each cartridge 104, 106 and patient needle assembly 120, with a valved, anti-backflow, medication mixing chamber defined therebetween.

Figure 6:
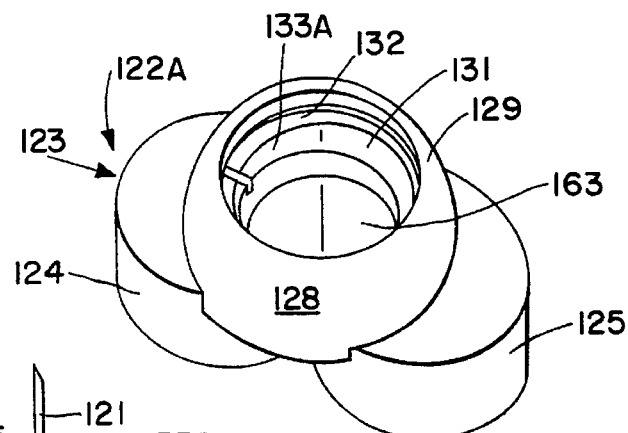
FIG. 6 is a perspective view of the manifold housing.
Figure 5:
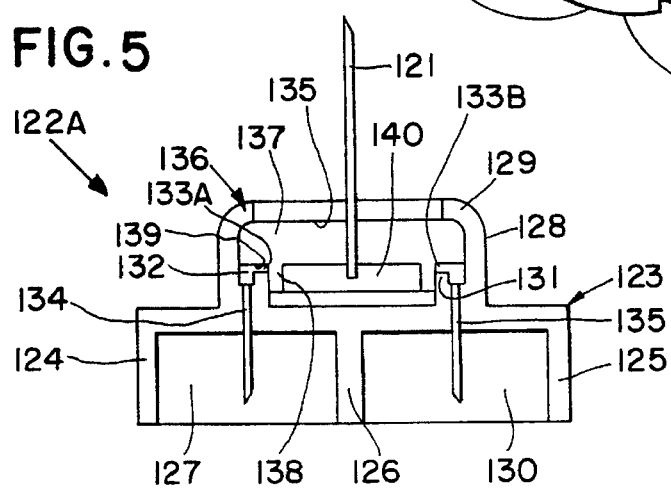
FIG. 5 is a sectional view of the manifold assembly.
Figure 12B:
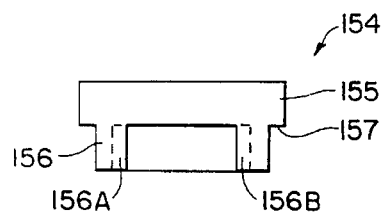
FIG. 12B is a sectional view of the flapper valve of FIG. 12A taken along line 12B—12B thereof.
Figure 12A:
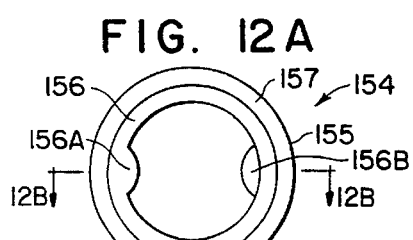
FIG. 12A is a plan view of an alternative embodiment of a flapper valve.

Referring now to FIGS. 5 and 6, there is depicted an embodiment of a manifold assembly 122A. Manifold assembly 122A includes a housing 123 having a first cylindrical portion 124, a second cylindrical portion 125, and a third cylindrical portion 128 all integrally formed as one piece of, for example, an injection molded plastic. First cylindrical portion 124 and second cylindrical portion 125 share a common wall 126 thereby defining respective chambers 127, 130 each of sufficient diameter to fit over necks 109, 111 of respective cartridges 104, 106. Radially inside third annular portion 128 and axially above chambers 127, 130, is an integrally formed annular ledge 131 having an annular channel or groove 132 with notches 133A, 133B formed therein. A cannula 134 extends from chamber 127 into channel 132, while a cannula 135 extends from chamber 130 into channel 132 at a location diametrically opposite where cannula 134 communicates with channel 132. Each cannula 134, 135 provides fluid communication between the medication contained in the cartridges 104, 106 and channel 132.

Third annular portion 128 defines an interior disc-shaped cavity 163 in which is placed an annular flapper valve and septum 136 made of, for example a butyl rubber. Additionally referring to FIGS. 7A, 7B, flapper valve 136 comprises a compressible solid disc-shaped portion 137 of an outside diameter slightly greater than the diameter of cavity 163. Radially inset from the outside annular edge of disc-shaped portion 137 is an annular skirt 138 axially downwardly extending from disc-shaped portion 137. Radially between annular skirt 138 and the outside annular edge of disc-shaped portion 137 is an annular underside portion 139. As best shown in FIG. 5, annular underside portion 139 and annular skirt 138 enclose annular channel 132 thereby defining a closed, annular fluid conduit. Radially inwardly from annular skirt 138 is a mixing chamber 140 defined by disc-shaped cavity 163 and valve 136. Patient needle 121 extends through disc-shaped portion 137 and into mixing chamber 140.

During injection of the medication from cartridges 104, 106, the liquid medication is forced out of the cartridges by plungers 105, 107 and into the respective cannulas 134, 135. The liquid medication travels upwardly through the cannulas and into channel 132. Pressure exerted by the liquid medication flowing through notches 133A, 133B causes the resilient skirt 138 to be pushed radially inwardly since annular underside 139 prevents further upward movement, thereby allowing the liquid medication to flow into mixing chamber 140. As depicted in FIG. 8, the portion 141 adjacent notches 133A, 133B deform radially inwardly to allow the liquid medication to flow into mixing chamber 140. However, once the radially inward pressure of the liquid medication ceases after injection, resilient skirt 138 returns to its original shape and closes off channel 132 from mixing chamber 140 by blocking notches 133A, 133B. The mixed medication is then caused to flow from mixing chamber 140 out of patient needle 121.

It is desirable to avoid allowing the opposite liquid medication from one cannula to enter the other cannula. This may be accomplished by utilizing some type of check valve. In this regard, alternative flapper valves are described hereinbelow with reference to appropriate figures.

Figure 13B:
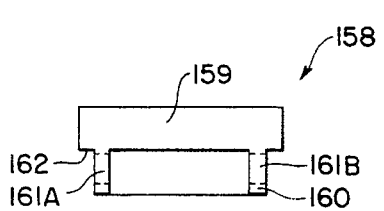
FIG. 13B is a sectional view of the flapper valve of FIG. 13A taken along line 13B—13B thereof.
Figure 13A:
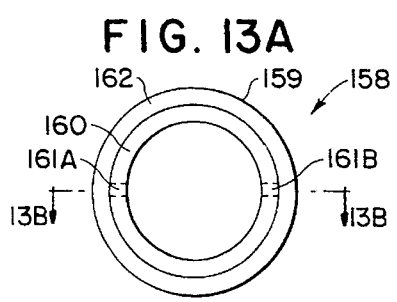
FIG. 13A is a plan view of an alternative embodiment of a flapper valve.

Referring to FIGS. 9A, 9B–13A, 13B there are shown alternative forms of a flapper valve which can be utilized with manifold assembly 122A. FIGS. 9A and 9B depict a butyl rubber flapper valve 142 having a solid disc-shaped portion 143 with an axially downwardly extending skirt 144 that radially inwardly tapers. An annular underside portion 145 is defined radially between skirt 144 and the outside edge of disc-shaped portion 143. In this form, tapered flapper valve 142 will open with less fluid pressure. FIGS. 10A and 10B depict a butyl rubber flapper valve 146 having a solid disc-shaped portion 147 with an axially downwardly extending skirt 148 that radially inwardly tapers and which is radially undercut. An annular underside portion 149 is defined radially between skirt 148 and the outside edge of disc-shaped portion 147. In this form, tapered and undercut flapper valve 146 will also open with less fluid pressure. FIGS. 11A and 11B depict a butyl rubber flapper valve 150 having a solid disc-shaped portion 151 with two axially downwardly extending skirt portions 152A and 152B. Skirt portion 152A is diametrically opposed to skirt portion 152B corresponding in position to the openings 133A, 133B in channel 132. In this form, liquid medication can travel around each skirt portion 152A and 152B and into mixing chamber 140. Such configuration will require less pressure for the liquid medication to flow thereabout from the cannula, but which also require less pressure to close. FIGS. 12A and 12B depict a butyl rubber flapper valve 154 having a solid disc-shaped portion 155 with an axially downwardly extending skirt 156. Two radially inwardly projecting lobes 156A and 156B are diametrically disposed on skirt 156 corresponding to a 90° offset in position relative to openings 133A, 133B in channel 132. In this form, lobes 156A, 156B retard the liquid medication from traveling around channel 132 and mixing with the other liquid medication. Lobes 156A, 156B require more pressure to deform and thus provides a tighter sealing of channel 132 from mixing chamber 140. FIGS. 13A and 13B depict a fenestrated butyl rubber flapper valve 158 having a solid disc-shaped portion 159 with an axially downwardly extending annular skirt 160. An annular underside portion 162 is defined radially between skirt 106 and the outside edge of disc-shaped portion 159. Two diametrically opposed grooves 161A and 161B are disposed in annular skirt 160 corresponding to a 90° offset in position relative to openings 133A, 133B in channel 132. In this form, the liquid medication flows from grooves 161A, 161B into mixing chamber 140.

Figure 14:
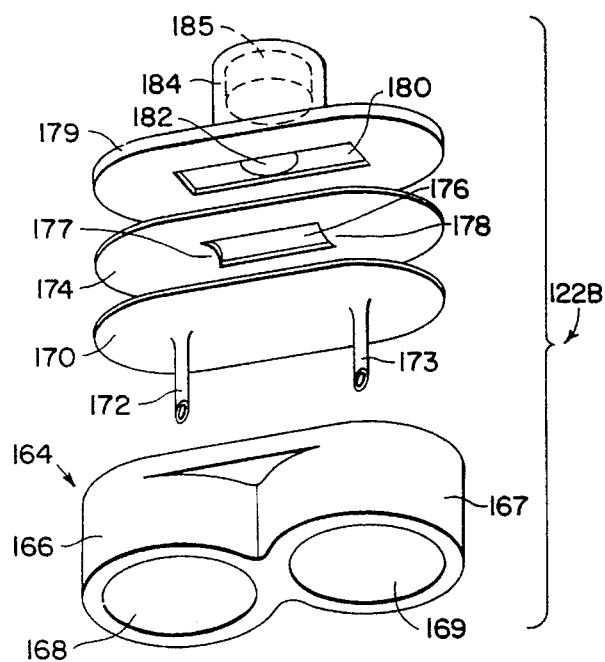
FIG. 14 is an exploded perspective view of an alternative embodiment of a manifold assembly.

Referring now to FIG. 14 there is shown an alternative embodiment of manifold assembly 122 having a double deep drawn needle and manifold assembly 122B. Manifold assembly 122B includes a plastic manifold housing 164 having a first cylindrical portion 166 defining a disc-shaped cavity 168 and a second cylindrical portion 167 defining a disc-shaped cavity 169. Cavities 168, 169 generally correspond in diameter to the diameter of necks 109, 111 of cartridges 104, 106 such that manifold housing 166 fits thereover. An elongated oval-shaped stainless steel plate 170 having two integral deep drawn needles 172, 173 is received in manifold housing 166 such that needles 172, 173 are centrally positioned within respective cavities 168, 169. Such integral deep drawn needles are generally fashioned from a single, flat piece of stainless steel. The needles are formed by slowly drawing or stretching the stainless steel at the desired locations of the needles until the desired length is achieved, Integral needles advantageously eliminate bothersome two-piece needle/plate assemblies.

When manifold assembly 122B is in place on body 102 of injector 100, needles 172, 173 extend through the rubber stoppers or seals and into respective cartridges 104, 106. An elongated oval-shaped butyl rubber septum 174 having a rectangular opening 176 is received in rear manifold housing 164 over plate 170. Septum 174 includes two semi-annular flaps or value portions 177, 178 that extend from the short sides into opening 176 directly axially above needles 172, 173. Thus, as fluid pressure increases from expulsion of liquid medication from the respective cartridges, flaps 177, 178 will displace such that the liquid medication will flow into opening 176. As fluid pressure is relieved, flaps 177, 178 close over the needle openings (not shown). An elongated oval-shaped housing 179 made of a suitable plastic is received axially over septum 174 and inside manifold housing 164. Housing 179 includes a rectangular channel 180 in communication with opening 176 and a bore 182 in communication with cylindrical portion 184. Received inside cylindrical portion 184 is a rubber bung 185 for receiving a patient needle.

Figure 15:
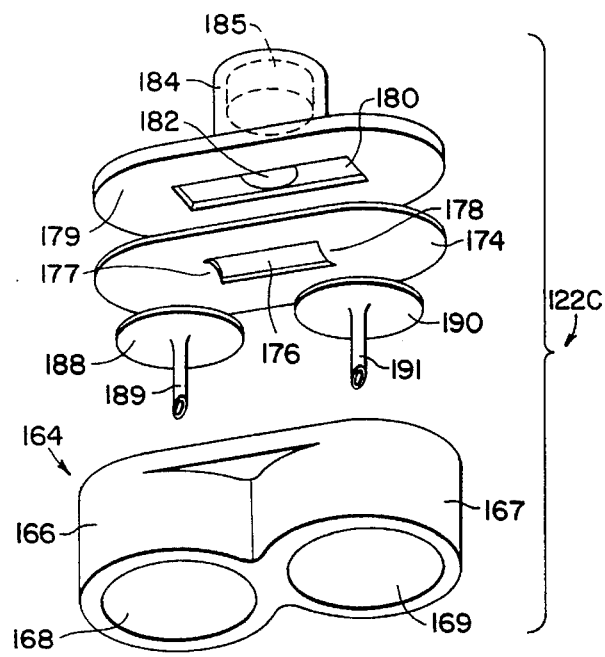
FIG. 15 is an exploded perspective view of an alternative embodiment of a manifold assembly.

The manifold assembly 122C depicted in FIG. 15 is identical in form and function to manifold assembly 122B depicted in FIG. 14 with the exception of the form of the cartridge cannulas. Manifold assembly 122C includes two stainless steel plates 188 and 190 each having a single drawn cannula 189, 191 respectively.

Figure 16:
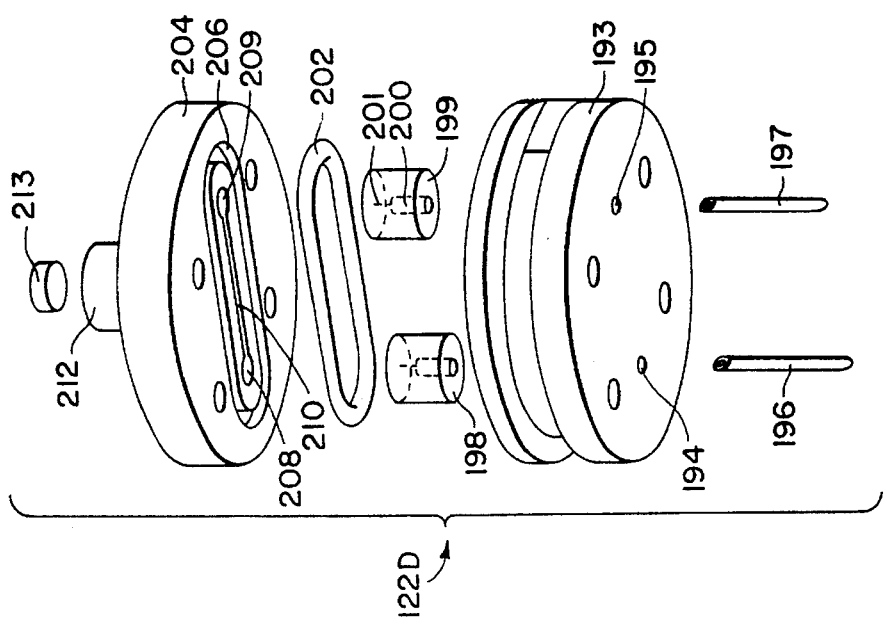
FIG. 16 is an exploded perspective view of an alternative embodiment of a manifold assembly.

FIG. 16 depicts another alternative embodiment of a manifold assembly 122D. A disc-shaped plastic housing 193 includes two cannula bores 194, 195 in which are received respective cannulas 196, 197. Cannula bores 194, 195 and thus cannulas 196, 197 are positioned such that they will provide fluid communication with cartridges 104, 106 of injector 100. Cannulas 196, 197 extend through manifold housing 193 and are received in solid butyl rubber plugs 198, 199 which are received in respective bores (not shown) in housing 193. Plugs 198, 199 act as valves to prevent the backflow of liquid medication. This is accomplished in the following manner with reference to plug 199. As cannula 197 is inserted through cannula bore 195 of housing 193, cannula 197 is caused to travel completely through plug 199. This creates a collapsed lumen, or rupture 201 along an axis of plug 199. Cannula 197 has, for example, a $\phi$ of 0.020" while in the closed state, collapsed lumen 201 has a $\phi$ of 0.0". Cannula 197 is then drawn back a distance such that the end is within plug 199 in the area designated 200. Collapsed lumen 201 acts like a duckbill valve to spread, such that $\phi$ is greater than 0.0" and allow liquid medication to pass through from cannula 197 when adequate liquid pressure is developed, but which retards backflow by closing in on itself back to a $\phi$ of 0.0".

Manifold assembly 122D further includes an elongated oval-shaped O-ring 202 which is received in a like channel 206 formed in manifold 204 in order to prevent leakage. Manifold 204 is received in manifold housing 193 and includes two valve alignment bores 208, 209 corresponding in position to cannulas 196, 197, and are in communication with each other via channel 210 formed therebetween in manifold 204. Channel 210 functions as a mixing chamber for the liquid medication and is in communication with cylindrical opening 212 in which is received a rubber bung 213 for receiving a patient needle (not shown).

Figure 17:
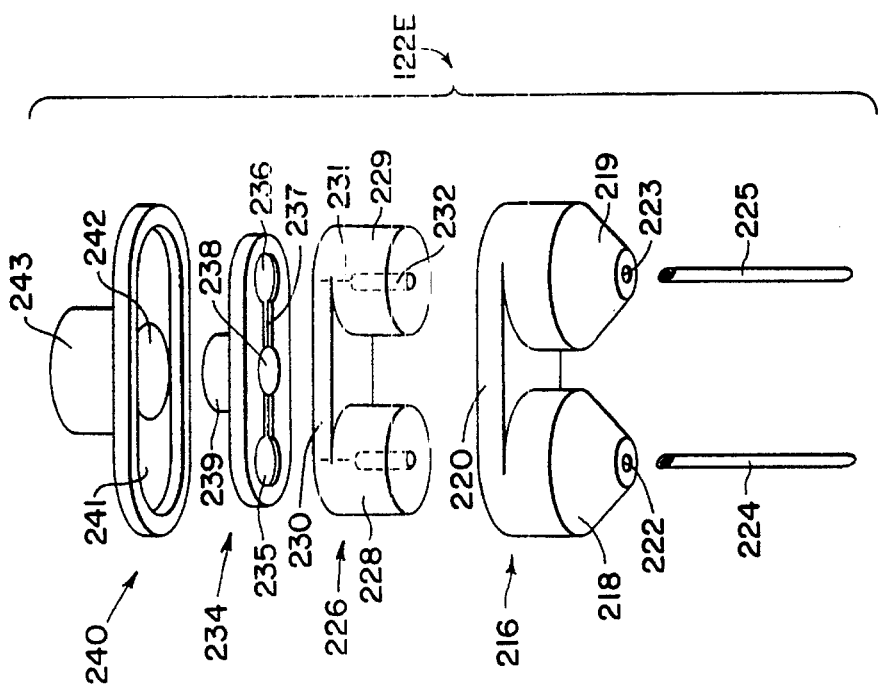
FIG. 17 is an exploded perspective view of an alternative embodiment of a manifold assembly.

Referring to FIG. 17, there is shown another alternative embodiment of a manifold assembly designated 122E. Manifold assembly 122E is similar in structure to manifold assembly 122D except that the valve and septum are both of solid butyl rubber, a material that is FDA approved for insulin contact. A plastic housing 216 having two conical portions 218, 219 is joined by a plate portion 220 extending therebetween. Each conical portion 218, 219 has a respective cannula opening 222, 223 in which is received a respective cannula 224, 225. Received in housing 216 is a butyl rubber check valve body 226 having first and second solid cylindrical portions 228, 229 connected by a plate portion 230 therebetween. First and second cylindrical portions 228, 229 define a check valve, with a puncture 231 and cannula bore 232 formed therein in like manner to the plug/valves 198, 199 of FIG. 16. Cylindrical portions 228, 229 also function in like manner to plug/valves 198, 199 of FIG. 16. Disposed axially above valve body 226 and partially received in housing 216 is an elongated oval-shaped butyl rubber septum 234 having first and second annular depressions 235, 236 in axial alignment with cannulas 224, 225 and the fluid flow path. A channel 237 extends between annular depressions 235, 236 and together form a mixing chamber for the liquid medication. Centrally disposed in channel 237 is a bore 238 extending to a solid cylindrical portion 239. Axially above septum 234 is a plastic needle body 240 having an elongated oval-shaped depression. 241 which corresponds in size to the outside dimensions of septum 234 so as to fit thereover. Cylindrical portion 239 is received in a bore 242 and hollow cylindrical portion 243. A patient needle extends into cylindrical portion 243 and into solid rubber cylindrical portion 239 such that the patient needle is in fluid communication with channel 237.

Figure 18:
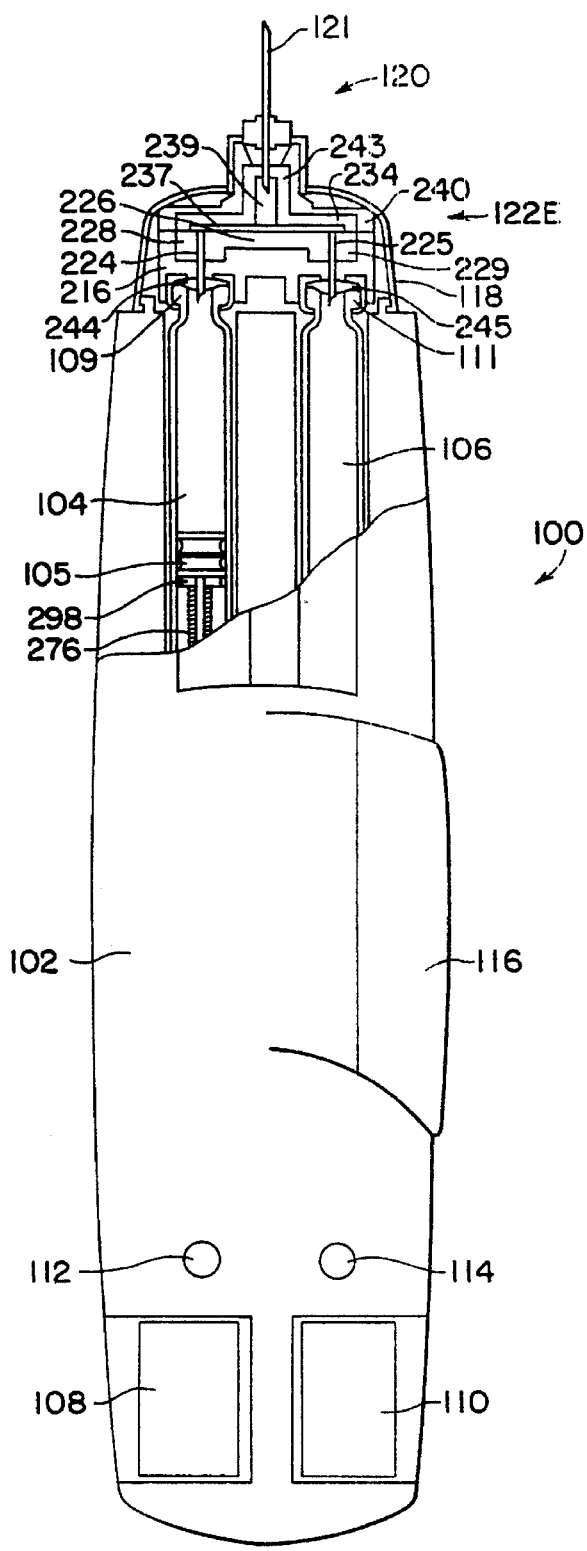
FIG. 18 is a partial sectional view of the injection apparatus of FIG. 1 incorporating the manifold assembly of FIG. 17.

The manifold assembly of FIG. 17 is shown in FIG. 18 as utilized in injector 100. Manifold assembly 122E is housed in manifold cap 118 and placed over the cartridge end of injector 100. Since necks 109, 111 of cartridges 104, 106 extend beyond a plane defined at the cartridge end of body 102 and perpendicular to the longitudinal axis of body 102 (see FIG. 3), the placing of manifold assembly 122E with cannulas 224, 225, causes cannulas 224, 225 to pierce disk seals or membranes 244, 245 of cartridges 104, 106. In this manner, the liquid medication contained within the cartridges will flow into the respective cannulas, through the appropriate valve(s), mix, and be discharged via the patient needle during injection.

Figure 60:
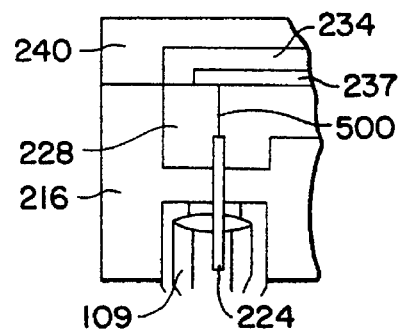
FIG. 60 is an enlarged partial sectional view of the butyl rubber check valve body and cannula of FIG. 18.

FIG. 60 shows that, like the valves of FIGS. 16 and 17, body 228 includes a collapsed lumen 500 which, in the closed state, has a $\phi$ of 0.0". Thus, Body 228 functions as a duck-bill valve to prevent backflow of mixed and unmixed insulin into the cartridges.

Having hereinabove thus described the manner and form in which the insulin, contained within each cartridge, is caused to mix without cross-contamination, and be discharged via a single cannula during injection, attention is now drawn to the manner and form of the metering, loading, injecting, and resetting mechanism of the wing-type dual medication injector 100.

Figure 19:
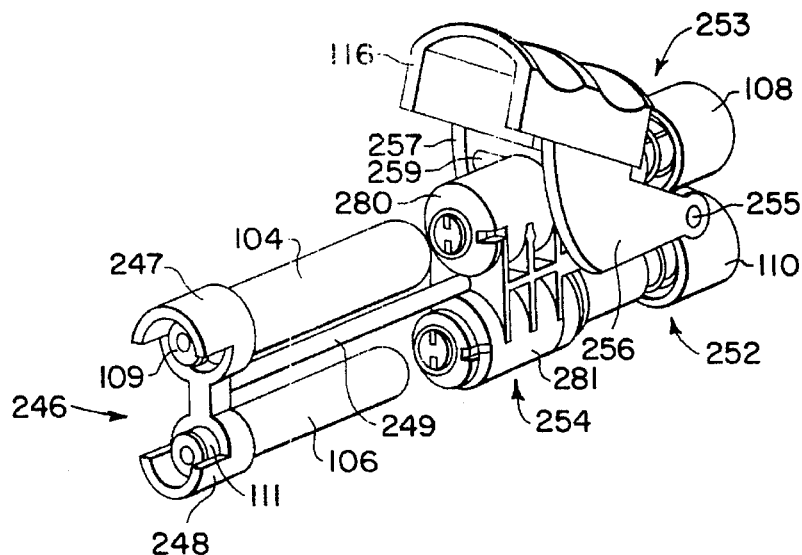
FIG. 19 is a perspective view of the internal assembly of the injection apparatus of FIG. 1.
Figure 20:
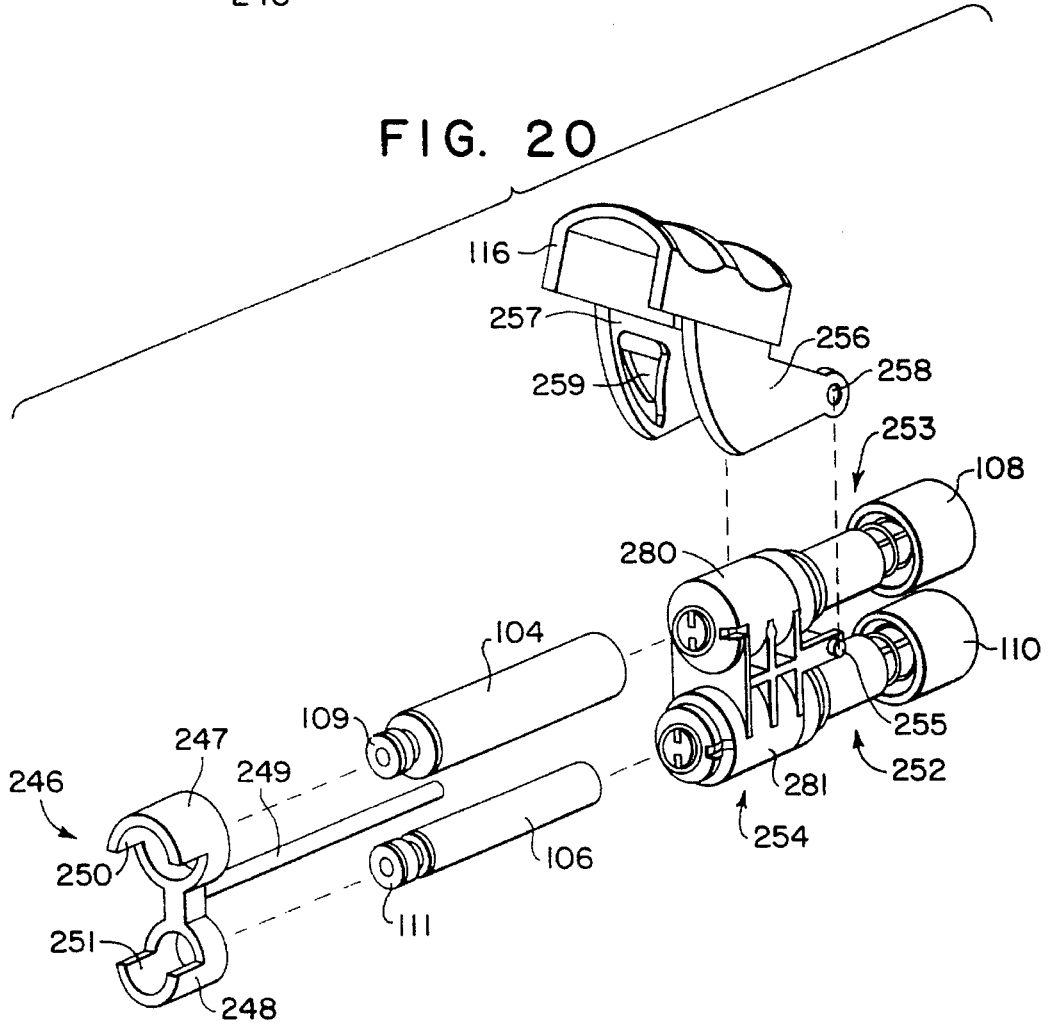
FIG. 20 is an exploded perspective view of the internal assembly of FIG. 19.

With reference to FIGS. 19 and 20, the internal, working mechanism of injector 100 will now be described. Retainingly holding cartridges 104, 106 within body 102 is a cartridge/manifold holder 246 having two appropriately sized, connected annular guides 247, 248. Holder 246 maintains necks 109, 111 of cartridges 104, 106 in the proper orientation for penetration by the dual cannulas as described hereinabove. A stem 249 of holder 246 longitudinally extends from guides 247, 248 towards shuttle or carrier 254, for maintaining the proper spacing between cartridges 104, 106 and shuttle 254. Shuttle 254 holds two metering/injecting mechanisms 252, 253, one metering/injecting mechanism for each cartridge 104, 106. Wing 116 includes two elbowed side flanges 256, 257 each terminating with a pivot bore 258 (only one shown) in which a pair of pivot pins (not shown) on housing 102 fit. Wing 116 is thus pivotable upward and outward from shuttle 254. This wing motion, along with track 259, provides the loading and injecting motion for shuttle 254.

In further detail, and referring now to FIGS. 21 and 22, the shuttle and metering mechanism will be described. Shuttle 254 is a plastic, one-piece, structure forming two cylindrical shells 280, 281 each having at one end a restricted opening 282 with rearwardly facing teeth 283 annularly spaced about the inside diameter of restricted opening 282. Opening 284 at the end distal restricted opening 282 is of sufficient diameter so as to accept metering mechanism 252.

All of the components of metering mechanism 252 are shown in FIG. 22, and include longitudinally extending metering dial 260 with metering knob 110, helical return spring 262, cylindrical dose indication dial, annular lockring 266, cylindrical pusher 268, cylindrical shuttle sleeve 270, drive nut 272, pullback spring (elastomeric washer) 274, leadscrew 276, and pullback nut 278. Each basic component, described in detail hereinbelow, cooperates with selective other components to achieve bi-directional dosage metering for each cartridge, as well as dosage indication, injection, and retraction/resetting.

It should be first understood that the metering mechanism 253 is identical in form and function to metering mechanism 252, and that the following description referencing metering mechanism 252 is likewise applicable to metering mechanism 253. Furthermore, the following FIGS. 23–28 depict only those components relevant to the specific function being described in connection therewith.

Referring now to FIG. 23, there is shown an exploded view of those components of metering mechanism 252 forming the fundamental function of injector 100, i.e. the metering of a dosage of insulin or other medication. Metering dial 260 includes a longitudinal body 285 with metering knob 110 at one longitudinal end thereof. Body 285 is hollow and includes therein longitudinally extending internal splines 286. Drive nut 272 includes a disk 288 having a ring of axially extending teeth 289 on one side thereof. A longitudinal body 290 extends from the teeth side of disk 288 and includes external splines that mate with internal splines 286 of metering dial body 285 such that drive nut 272 is longitudinally translatable within metering dial 260 but is prevented from rotation relative to metering dial 260. An internally tapped, bore 292, having, for example a 28°–45° helix thread 295 therein, extends through disk 288 and body 290. Leadscrew 276 includes an externally threaded body 294 (see FIG. 24) having at the end proximate meter knob 110 an end cap 296, and at the end distal metering knob 110 a plunger disk 298. Disk 298 has two grooves 299, 300 disposed at an 180° interval that extend along the entire longitudinal length of body 293 in addition to the external threads. Pullback nut 278 comprises a ring 302 having axially extending teeth 304 disposed about the outer end thereof, and two anti-rotation projections 305, 306 extending radially inwardly from the inner surface of ring 302 into grooves 298 and 300.

Referring to FIG. 24, the components of FIG. 23 are shown in a sectional view. As indicated by the arrows, the turning of metering knob 110 is bi-directional such that leadscrew 276 translates forward and backward. This allows the user to change the dosage without insulin waste. As schematically illustrated in FIG. 24 drive nut 272 and pullback nut 278 are fixed to shuttle 254 which is stationary. Thus, by turning metering knob 110, metering dial 260 transmits the produced torque through the splines to rotate drive nut 272. Since drive nut 272 is essentially locked to shuttle 254 and therefore cannot move axially relative thereto, drive nut 272 rotates causing leadscrew 276 to longitudinally translate due to the threaded connection therebetween. Pullback nut 278 is likewise locked to shuttle 254 so as to prevent rotation and translation thereof. Plunger disk 298 longitudinally moves to make contact against cartridge plunger 107. Also, end cap 296 and drive nut 272 form an insufficient dosage lockout to limit the metering of the dosage to a certain amount as the cartridge empties. When leadscrew 276 translates in the forward direction end cap 296 will contact the end of drive nut 272 such that leadscrew 276 cannot travel any further. This lockout feature is important since when the plunger in the cartridge is at a certain depth, the volume of insulin inside the cartridge diminishes due to the curvature of the cartridge. The metering is thus stopped when the volume of insulin is less that the maximum metering setting.

Figure 25:
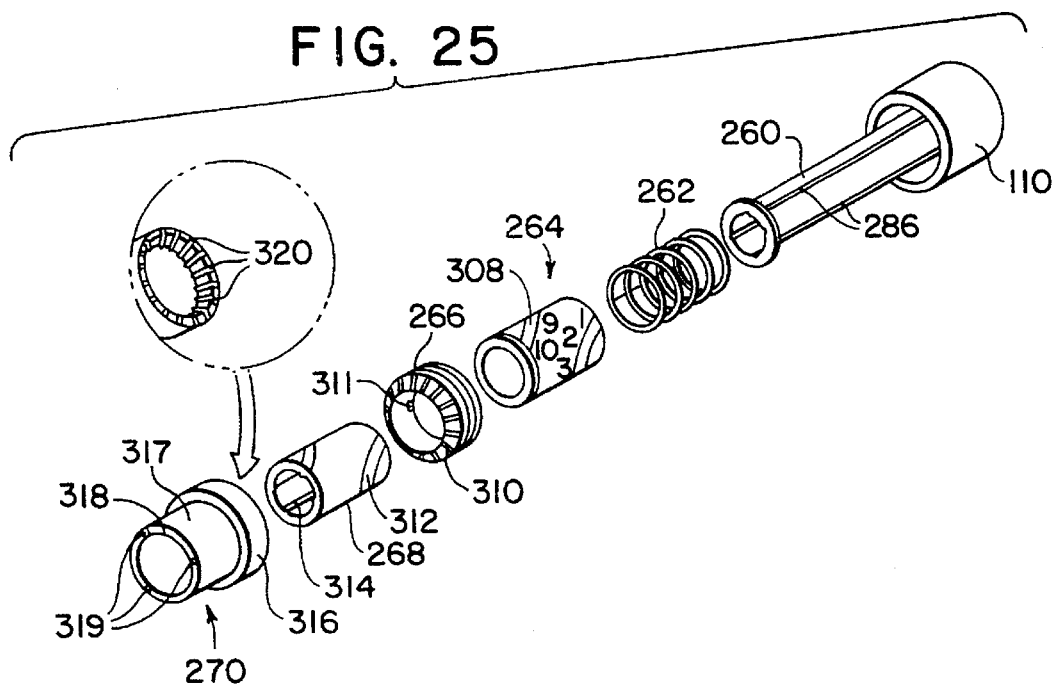
FIG. 25 is an exploded perspective view of another portion of the metering mechanism of FIG. 22.
Figure 26:
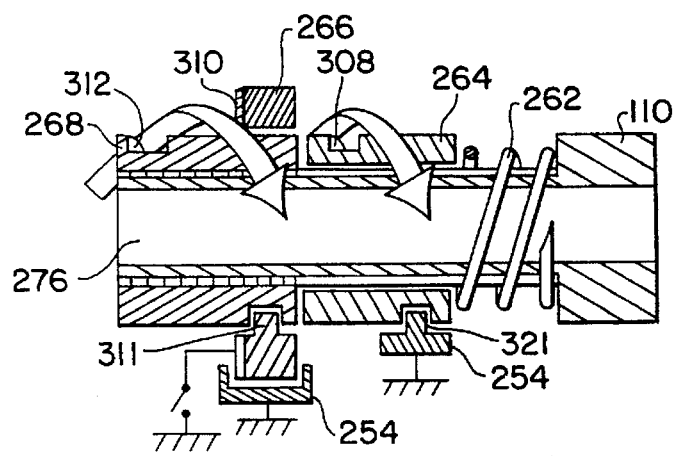
FIG. 26 is an enlarged sectional view of the portion of the metering mechanism shown in FIG. 25.

Referring now to FIGS. 25 and 26, the components for the loading and dosage indication functions are depicted. It should be noted that the dosage indication system serves to limit the metering, for example between 0 and 50 units per dose. Seated about metering dial 260 is a return spring 262 which when compressed between dose indicator 264 and metering knob 110 tends to push dose indicator 264 away from metering knob 110. Dose indicator 264 is a barrel-like sleeve which likewise is disposed about metering dial 260. A cam-like helical groove 308 is formed in the outside surface of dose indicator 264 which forms a track for pin 321 in the housing which is depicted as fixed relative to the assembly by a "ground" connection. Axially adjacent dose indicator 264 is a barrel-like pusher 268 having internal splines 314 and a cam-like helical groove 312. Internal splines 314 of pusher 268 are keyed to splines 286 of metering dial 260. Groove 312 forms a track for pin 311 of lockring 266 which is selectively fixed to shuttle 254 as described hereinbelow. Lockring 266 is thus selectively allowed to rotate but never translate. Lockring 266 is radially disposed about pusher 268 and includes an annular pattern of teeth 310 on a conical end portion thereof. Teeth 310 selectively engage teeth 320 of shuttle sleeve 270 which are disposed on an opposite-shaped conical portion inside first annular section 316 in order to provide selective rotation of lockring 266. Shuttle sleeve 270 is fixed to the shuttle such that shuttle sleeve 270 will not rotate, but will translate along with shuttle translation.

As best seen in FIG. 26, during metering, lockring 266 engages shuttle sleeve 270 such that lockring 266 cannot rotate. As metering dial 260 is rotated pusher 268 is caused to concurrently rotate and translate rearwardly since lockring 266 is fixed. The rearward translation pushes against dose indicator 264 which likewise concurrently rotates and translates rearwardly compressing return spring 262 against metering knob 110. Dose indication numbers on the outside surface of dose indicator dial 264 show a number in dosage window 114 indicative of the metered dosage.

FIG. 26 shows dose indicator 264 and pusher 268 in the forward translated position with the arrows indicating relative rotation thereof during translation. Return spring 262 will be compressed for returning dose indicator 264 and pusher 268 to a the Ready state or position.

Figure 27:
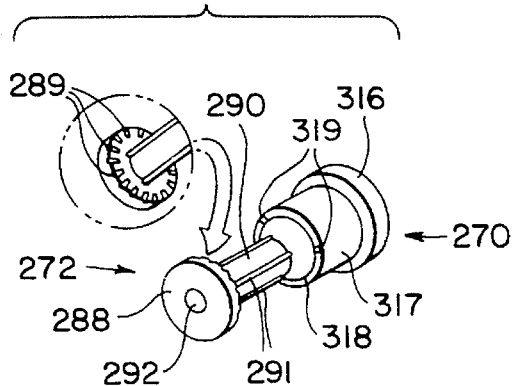
FIG. 27 is an exploded perspective view of another portion of the metering mechanism of FIG. 22.
Figure 28:
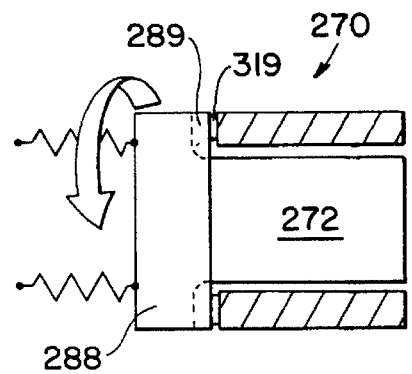
FIG. 28 is an enlarged sectional view of the portion of the metering mechanism shown in FIG. 27.

FIGS. 27 and 28 depict the tactile response feature provided by drive nut 272 and shuttle sleeve 270. As drive nut 272 is rotated through spline action with metering dial 260, notches 319 of shuttle sleeve 270 engage detents 289 of drive nut 272. There are 36 detents 289 each 10° apart, thereby providing one dosage resolution per 10°. Although such tactile response is not necessary to the metering function, it provides a feel to the metering process for the user.

The overall operation of the metering and injection process of the wing-type dual medication injection apparatus 100 will now be described with reference to FIGS. 29–39. It should be noted that the operation of only one metering assembly 252 will be described and depicted in FIGS. 29–34, but that metering assembly 253 is analogous thereto in function and operation. Also, it should be understood that disk 298 of leadscrew 276 is appropriately sized for contact with the respective cartridge, as one cartridge is a different diameter than the other cartridge. Furthermore, shuttle 254 has offset housings 280, 281 since the cartridges are different lengths.

Figure 29:
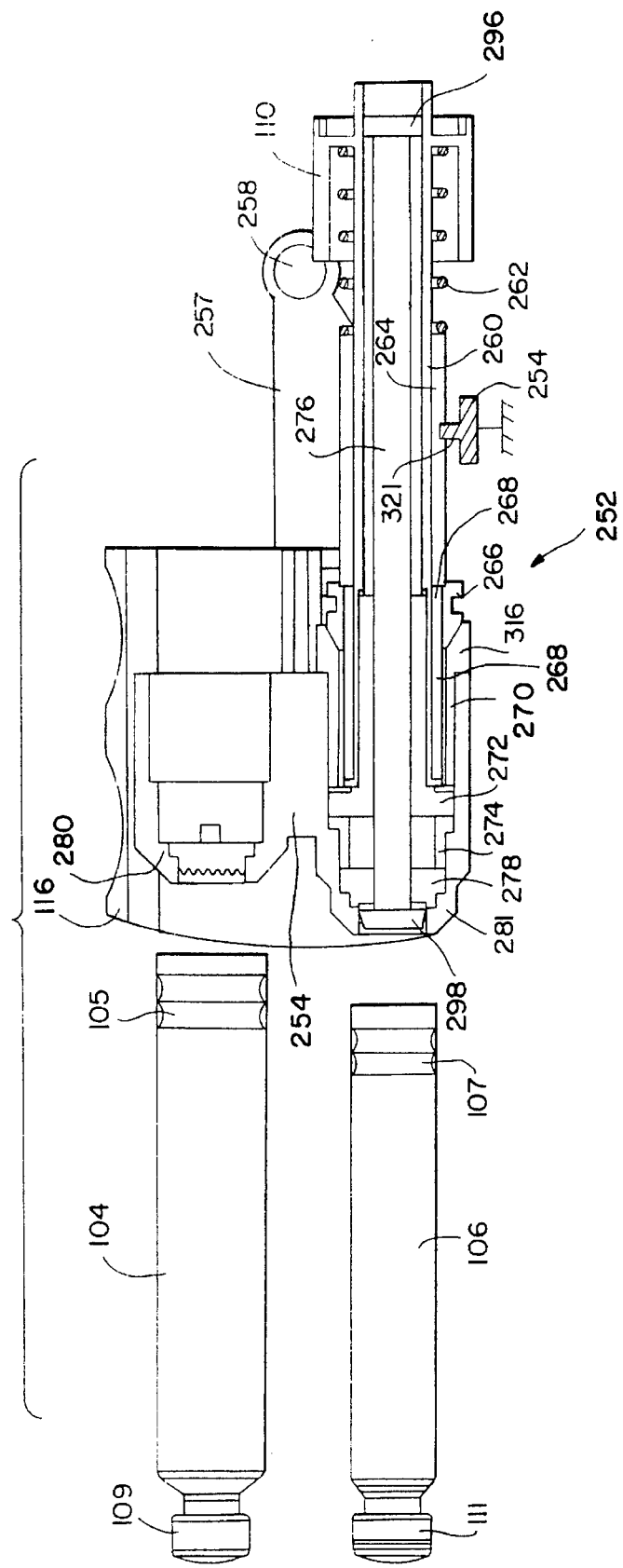
FIG. 29 is an enlarged sectional view of the metering and shuttle assembly of FIG. 19 in the Ready state.

Referring now to FIG. 29 measuring assembly 252 is in a Ready state ready for the metering process. Wing 116 is in a fully down position while leadscrew 276 is in a fully retracted position. All other components are in a steady state.

Figure 30:
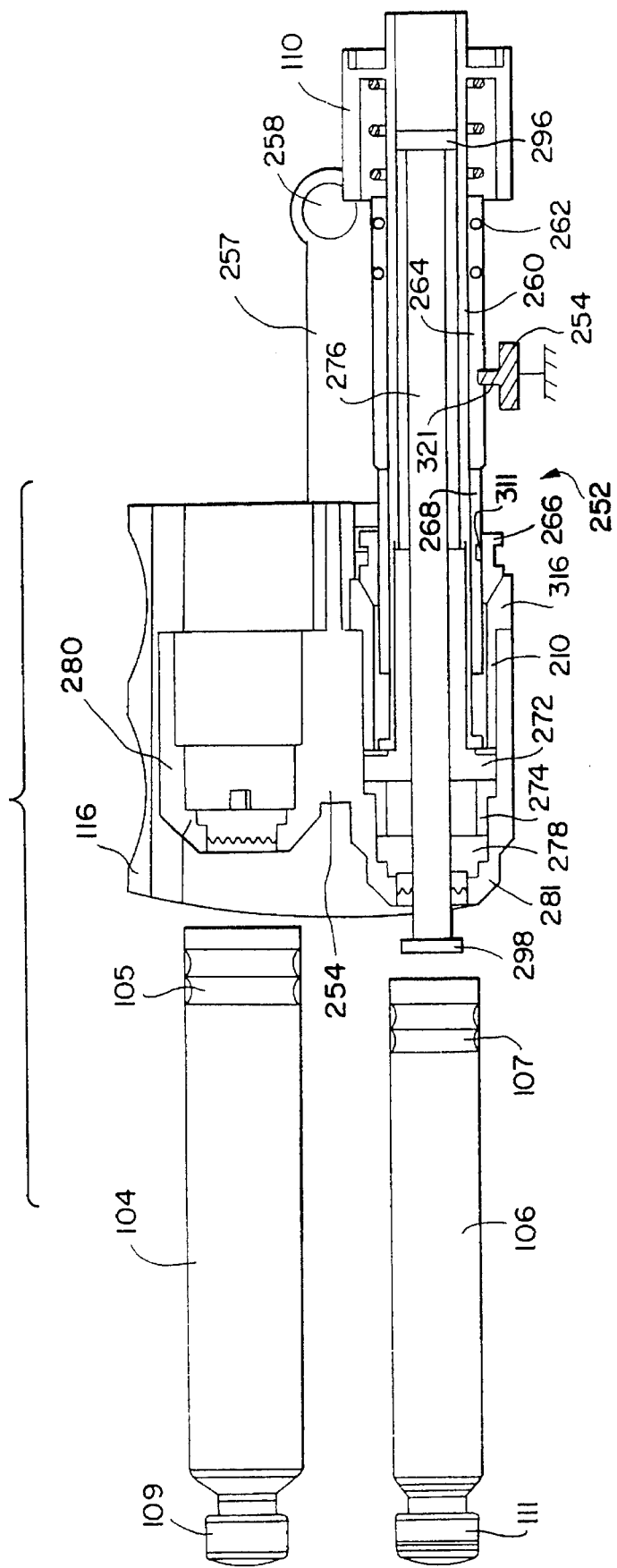
FIG. 30 is a sectional view of the metering and shuttle assembly of FIG. 19 in the Metering state.

FIG. 30 shows the metering process. Metering knob 110 is bi-directionally rotated which rotates metering dial 260 and in turn rotates drive nut 272. Rotation of drive nut 272 causes threaded leadscrew 276 to longitudinally translate depending on the direction of rotation of metering knob 110, while leadscrew 276 is kept from rotation by pullback nut 278 being fixed to shuttle 254 during metering. During metering, lockring 266 is locked from rotation by being in meshing engagement with shuttle sleeve portion 316 as shuttle sleeve 210 is fixed to shuttle 254. Rotation of metering dial 260 also tries to rotate pusher 268 as pusher 268 is splined with metering dial 260. However, because of the spline interface and pin 311 of lockring 266 in cam groove 312 of pusher 268, pusher 268 rotates and rearwardly translates. This rearward translation causes concurrent rotation and rearward translation of dosage indicator 264 since dosage indicator 264 is constrained by pin 321 and cam groove 308. This also compresses return spring 262 which now exerts a bias toward the cartridges.

Figure 31:
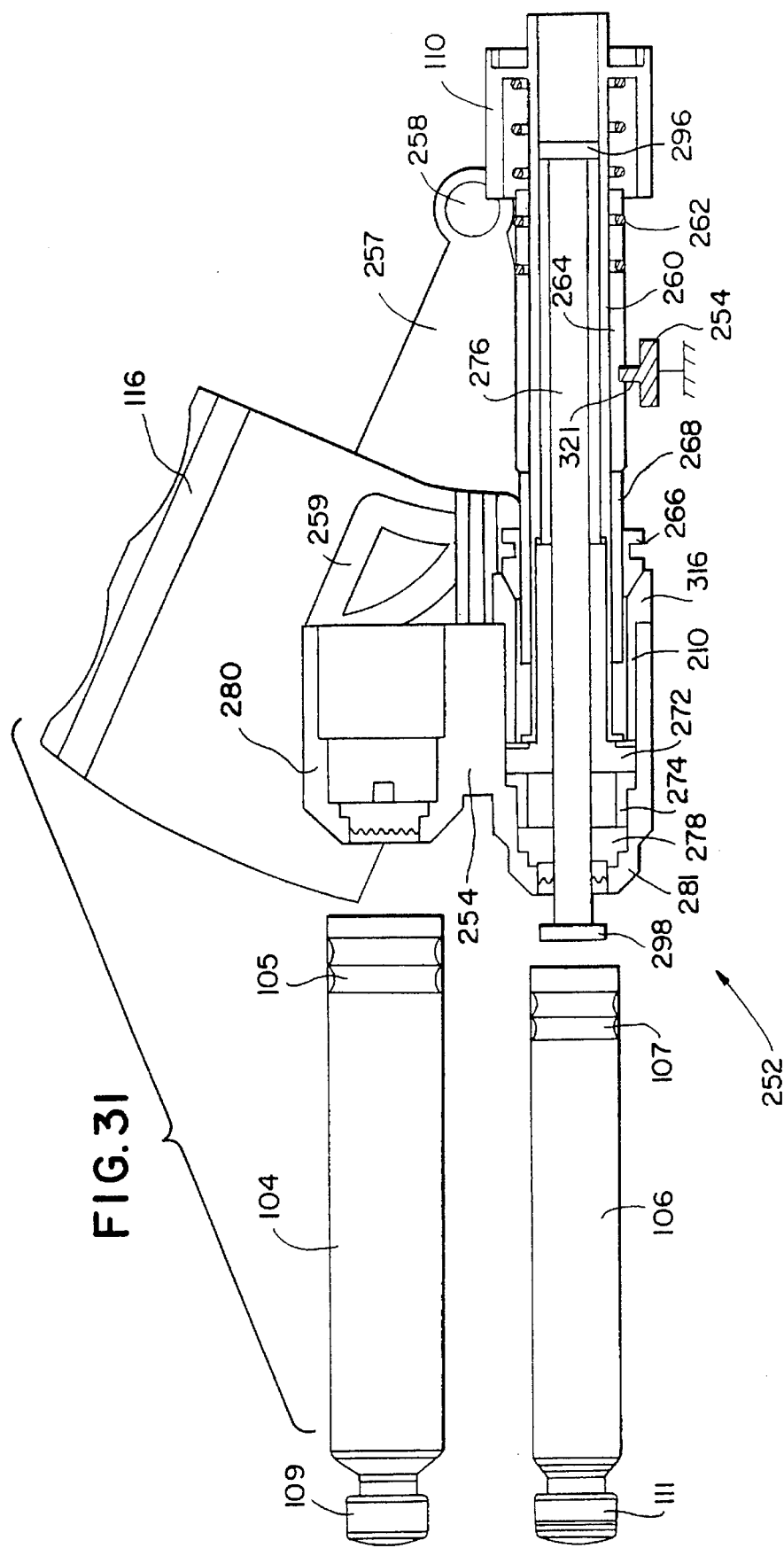
FIG. 31 is a sectional view of the metering and shuttle assembly of FIG. 19 in the Prepare To Inject state.

Referring now to FIG. 31 the assembly is now moved to the Prepare to Inject state. With leadscrew 276 projecting toward the cartridges a predetermined length corresponding to the dosage amount of the respective insulin cartridge, wing 116 is pivoted into a fully upward position, the mechanics of which will be described in detail hereinbelow. All the other components are in the position as depicted in FIG. 30.

The injection of the liquid medication by wing 116 and shuttle 254 develops a greater output force against the cartridge plunger for a given amount of input force to the wing. Injector 100 is gripped by the hand, and thus wing 116 is actuated by the natural inward motion of the fingers toward the palm. This motion provides a greater input force than a single finger exerting pressure upon the plunger of a conventional syringe.

Figure 32:
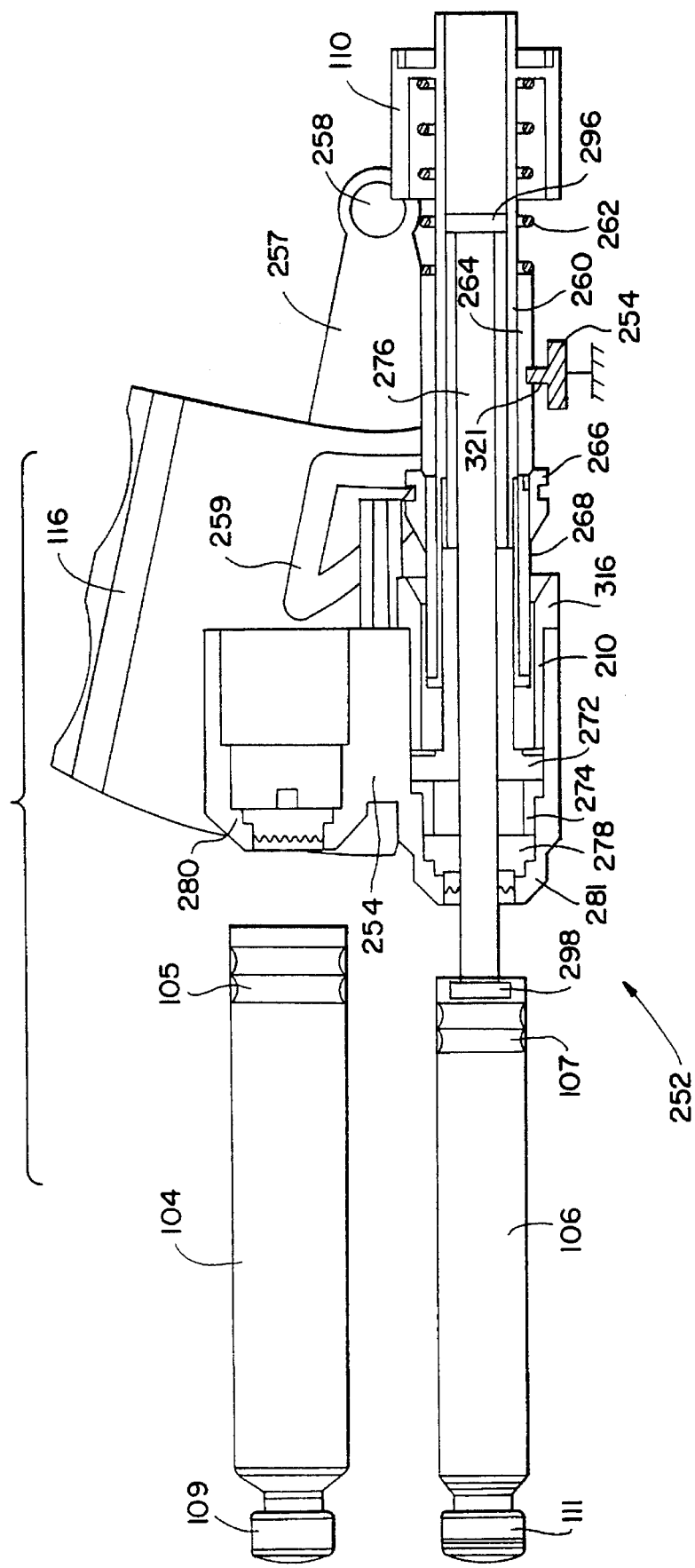
FIG. 32 is a sectional view of the metering and shuttle assembly of FIG. 19 in the Injection state.

FIG. 32 shows the Injection state as wing 116 is caused to be depressed by the fingers of the user pushing it downwardly. As wing 116 is pressed downwardly, pin 255 (not seen in FIG. 32) follows track 259, and being fixed relative to shuttle 254 causes shuttle 254 to forwardly advance. Forward advancement of shuttle 254 carries leadscrew 276, and pullback nut 278 therealong thereby pushing leadscrew 276 against plunger 107 to eject the dosage amount from cartridge 106. As shuttle 254 is carried forwardly, lockring 266 is disengaged from shuttle sleeve clutch 316 and is free to rotate. Return spring 262 provides a forward force to rotate and translate dosage indicator 264 to a reset position while also forcing against pusher 268 which, because lockring 266 is free to rotate, does not rotate but only forwardly translates toward the cartridges. Rotation of pusher 268 is not desirable as that would also rotate metering dial 260.

Head 298 of leadscrew 276 contacts against plunger 107 of cartridge 106, and with the force exerted through wing 166 and shuttle 254, the translation of leadscrew 276 causes plunger 107 to axially move within the cartridge, thereby expelling the liquid medication therefrom.

Figure 33:
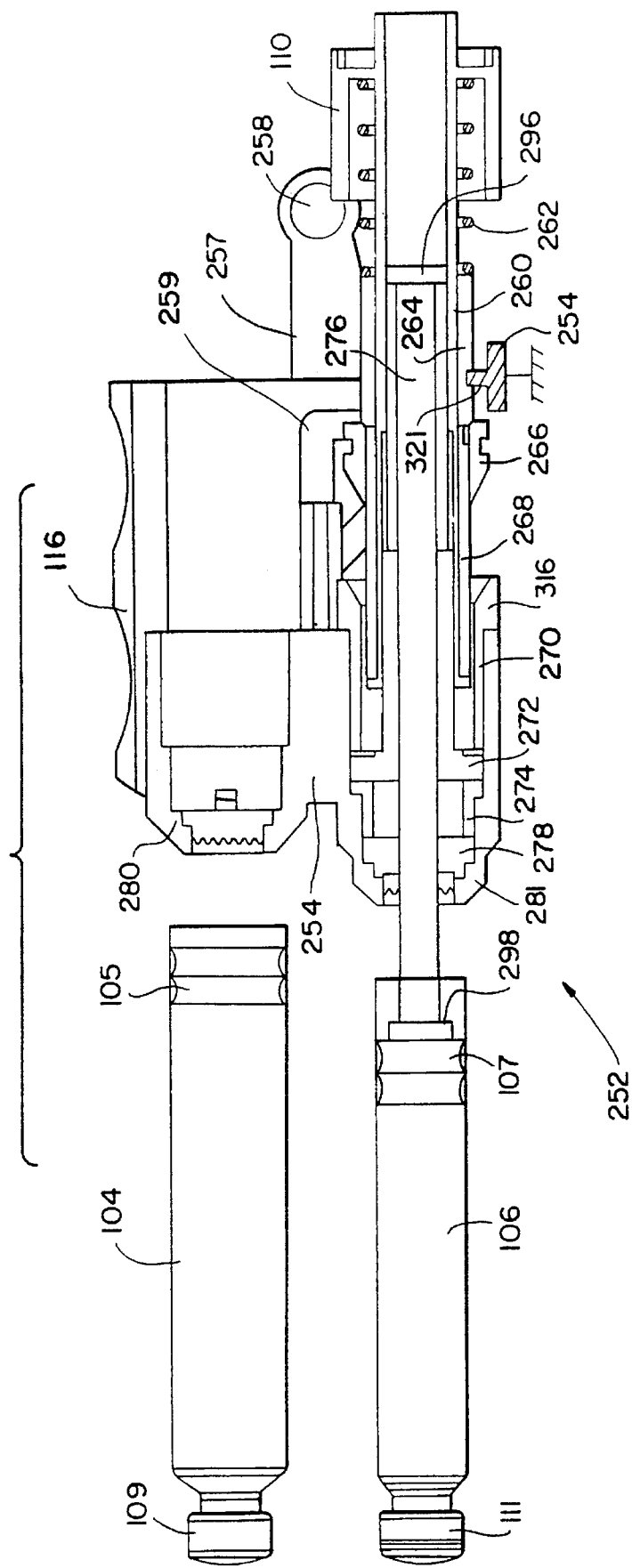
FIG. 33 is a sectional view of the metering and shuttle assembly of FIG. 19 in the End Of Injection state.

FIG. 33 shows shuttle 254 in a completely forward position, namely the end of injection state. Wing 116 is in a fully downward position and the injection of insulin is complete. All of the components of metering assembly 252 are as in FIG. 32.

Figure 34:
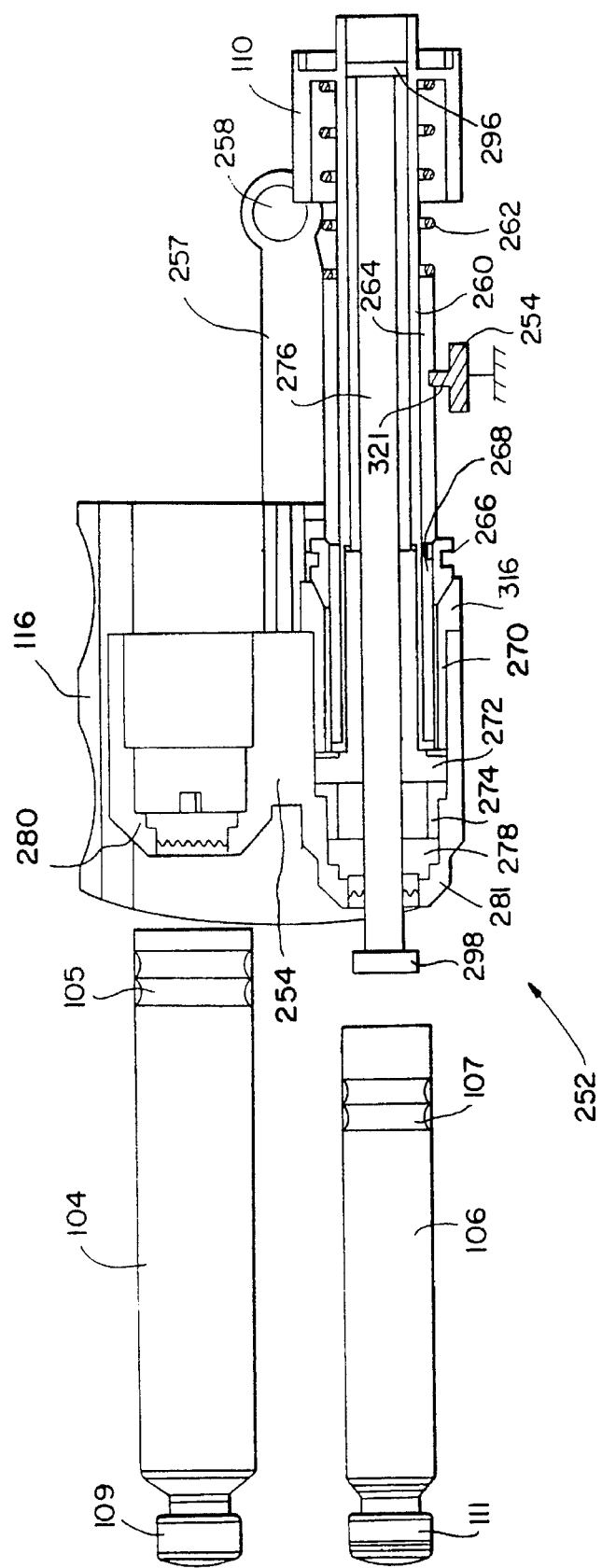
FIG. 34 is a sectional view of the metering and shuttle assembly of FIG. 19 in the Return To Ready state.

Referring now to FIG. 34, as soon as wing 116 is in its fully downward position and injection has taken place, leadscrew 276 has traveled the metered amount and remains in that position until the next metering sequence. Wing 116 is caused to pull shuttle 254 back into the steady state as depicted in FIG. 29.

The operation of wing 116 and its relationship to the movement of shuttle 254 will now be described with reference to FIGS. 35–39. A track 259 comprising three channels 324, 326, 328 form an essentially triangular path for pivot pin 255 is provided in one side 257 of wing 116. Pin 255 of shuttle 254 is disposed within track 259 and is connected to a compression spring 322. Compression spring 322 tries to exert a bias against pin 255, and thus against shuttle 254, to force shuttle 254 rearwardly.

Figure 35:
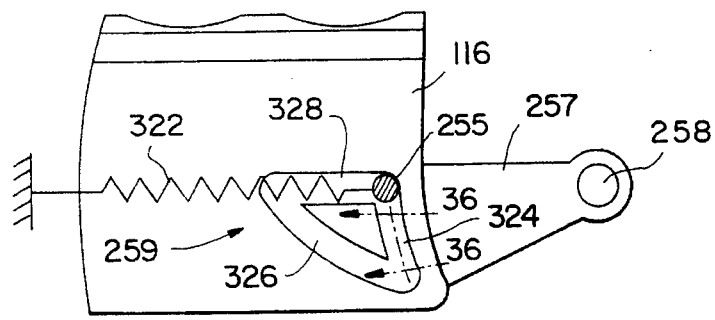
FIG. 35 is an enlarged diagrammatic view of the wing and track mechanism in the Ready and Metering state.
Figure 37:
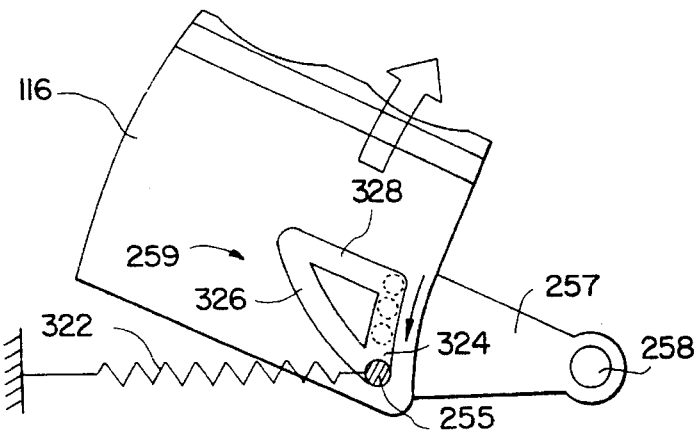
FIG. 37 is an enlarged diagrammatic view of the wing and track mechanism in the Prepare to Inject state.

Referring to FIG. 35, wing 116 is shown in the steady state position with pin 255 located at the intersection of channels 324 and 328 with compression spring 322 preventing wing 116 from translating forwardly. It should be noted that wing 116 is fixed from translation as pivot 258 is connected to fixed body 102. During this state, metering of the dosage is accomplished.

Figure 36:
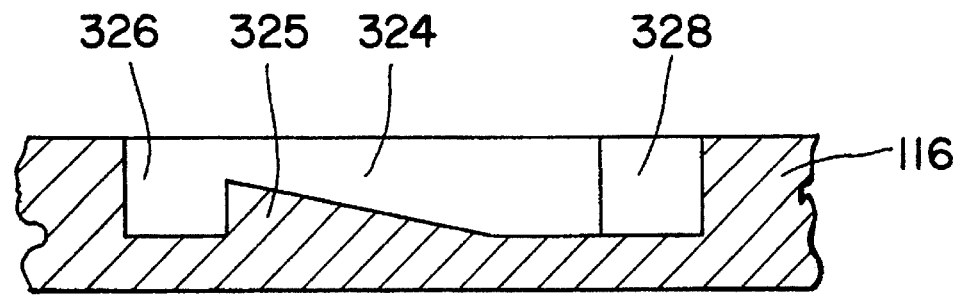
FIG. 36 is a sectional view of the ramp portion of the track mechanism taken along line 36—36 of FIG. 35.

After metering of the dosage is completed, the mechanism is set to inject. During the upward pull of wing 116, as represented by the arrow in FIG. 37, pin 255 is caused to move downwardly along track 324. As shown in FIG. 36 a ramp 325 in channel 324 causes pin 255 to remain in the position shown in FIG. 37 at the intersection of channels 324 and 326. At this point, wing 116 is fully upwardly extended, and is in the cocked position.

Figure 38:
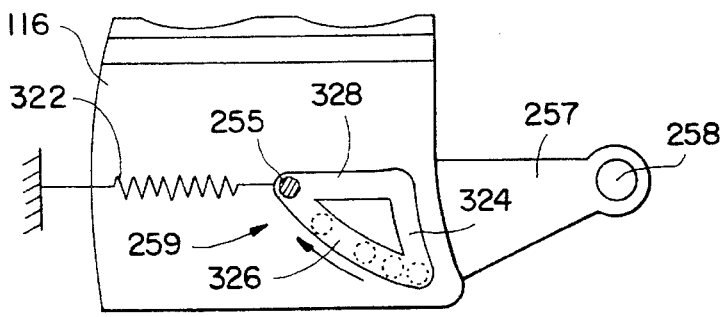
FIG. 38 is an enlarged diagrammatic view of the wing and track mechanism in the End of Injection state.

The injection stage is depicted in FIG. 38 in which wing 116 is pushed downwardly to pivot about pivot 258. Since channel 324 has ramp 325, pin 255 cannot travel back along channel 324 and thus is caused to travel along channel 326. This provides a forward translation of shuttle 254 the predetermined distance corresponding in length to the length of channel 328 in order to inject the insulin. Compression spring 322 provides a small amount of back pressure to the downward pivoting of wing 116. Further, compression spring 322 is loaded to force pin 255 and thus shuttle 254 back to the steady state upon pin 255 reaching the intersection of channels 326 and 328 which signifies the end of the injection.

Figure 39:
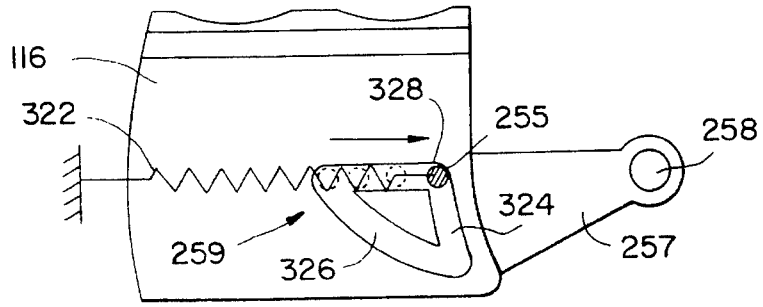
FIG. 39 is an enlarged diagrammatic view of the wing and track mechanism in the Return to Ready state.

Referring to FIG. 39, upon completing the injection, compression spring 322 forces pin 255 along channel 328 toward the steady state position as depicted in FIG. 35. Shuttle 254 is thus moved along with pin 255.

In summary, wing-type injector 100 is a hand-held device in which the wing/injection mechanism is controlled by a gripping action of the fingers. After the dose is set via dose knobs 108, 110, wing 116 is cocked. In the cocked position the user may then insert needle 121 into the body holding injector 100 with the hand. A gripping action by the fingers wrapping around wing 116 downwardly pushes wing 116 to inject the medications through concurrent action of shuttle 254 and the respective leadscrew. In the retracted position, wing 116 then advances to the Ready state.

Attention is now drawn to FIGS. 40 and 41 which depict another embodiment of the present invention referred to as the plunger-type dual medication injector 400. Injector 400 includes a main housing 402 having a cartridge end with the same type of cartridges 104, 106 and manifold, manifold cap 118, and needle assembly 120 as wing-type injector 100. As the cartridge, manifold, and needle assembly are the same for injector 400 as for injector 100, reference should be made to those figures and accompanying description for details of function and operation.

Injector 400 includes two metering knobs 404, 406 which bi-directionally meter the desired dosage amount into the respective metering mechanism. Housing 402 also includes dosage indicator windows 408, 410 for indicating the dosage metered by respective metering knobs 404, 406. At the distal end of cartridges 104, 106, injector 400 includes a plunger cap 412 that axially moves in response to user pressure during injection (FIG. 41), but which returns to a steady state by spring tension (FIG. 40). Plunger 412 includes a brake trigger 418 centrally disposed therein.

Figure 42:
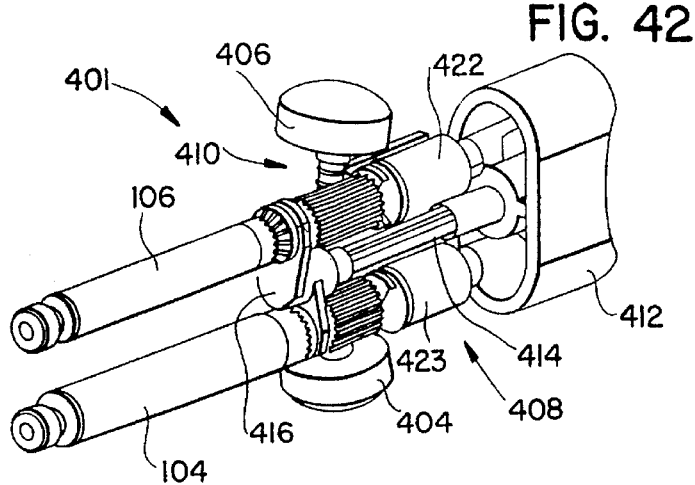
FIG. 42 is an elevational view of the internal assembly of FIG. 40.
Figure 43:
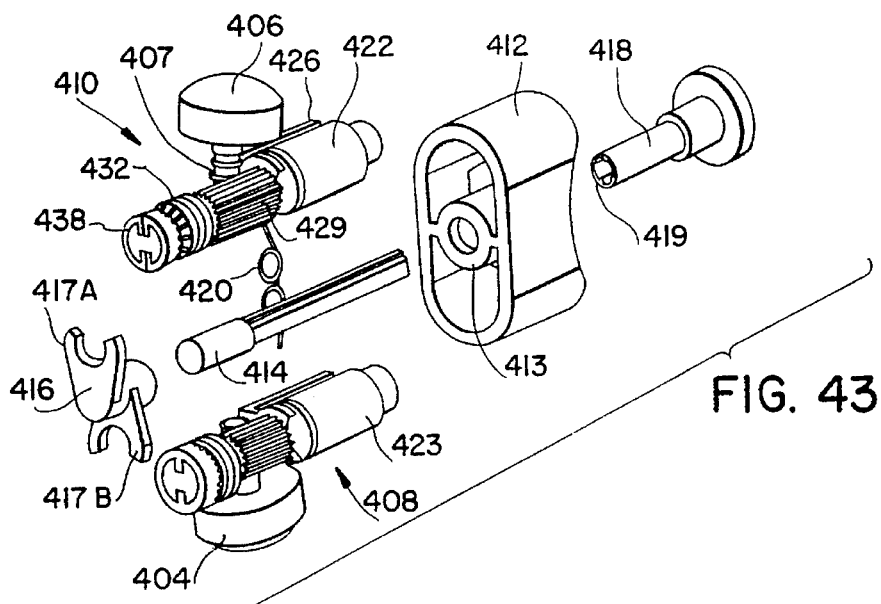
FIG. 43 is an exploded view of the internal assembly of FIG. 42.

Referring now to FIGS. 42 and 43, there is depicted the plunger and metering mechanism 401 of injector 400. FIG. 42 shows mechanism 401 in relation to cartridges 104, 106, which need to be in the correct holder in order for mechanism 401 to operate. This is achieved by matching the outside diameter of the cartridge to the holder and the inside diameter of the cartridge to the leadscrew head. It should be noted that this is the same for injector 100.

FIG. 42 shows the overall assembled mechanism 401 while FIG. 43 shows the same (except for cartridges 104, 106) in somewhat exploded fashion. Mechanism 401 includes two metering mechanisms 408, 410, a plunger 412, brake rod 414, brake arm 416, brake trigger 418, and power assist spring 420, each described in detail hereinbelow.

Figure 55:
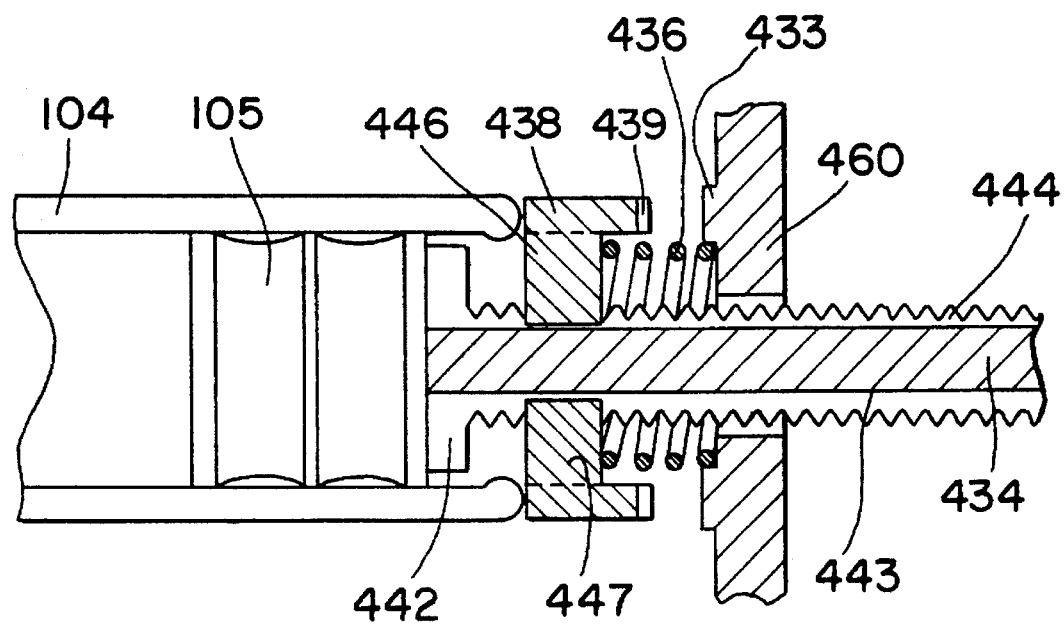
FIG. 55 is a sectional view of the pullback assembly of the metering device of FIG. 42.
Figure 44:
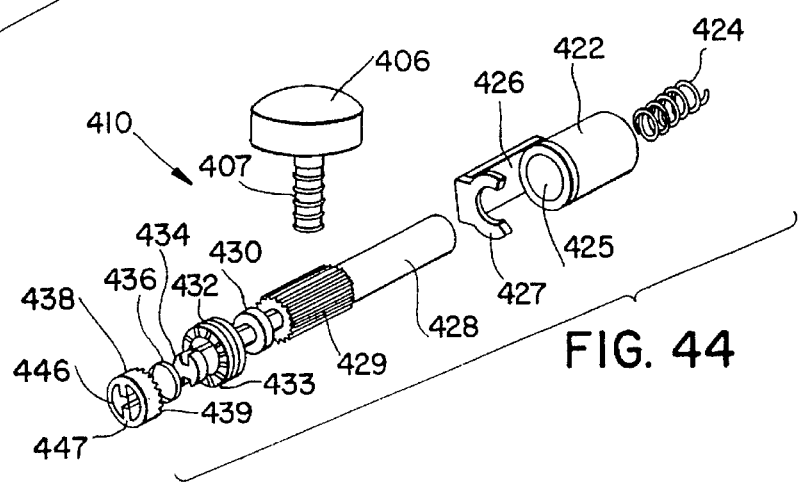
FIG. 44 is an exploded view of a single metering device of FIG. 42.

Referring now to FIG. 44 there is shown metering mechanism 410 in an exploded view. It should be understood that the operation of metering mechanism 408 is identical in form and function to metering mechanism 410, and thus the description of metering mechanism 410 is fully applicable to metering mechanism 408. Metering knob 406 includes a worm gear 407 that meshes with gear 429 disposed on one end of drive nut 428 such that rotation of metering knob 406 causes rotation of drive nut 428. Axially toward cartridges 104, 106, metering mechanism 401 further includes a brake spline 430 and brake clutch 432 both radially about leadscrew 434. Leadscrew 434 extends through pullback nut 438 with pullback spring 436 radially about leadscrew 434 between pullback nut 438 and brake clutch 432 (FIG. 55). Disposed towards the plunger axially behind drive nut 428 is a rack 426 having a retaining collar 427 that is disposed radially about drive nut 428 against gear 429 on one side and an end of dosage indicator dial 422. Drive nut 428 extends into opening 425 of dosage indicator dial 422 such that dosage indicator dial 422 is disposed radially thereabout. A return spring 424 is received within dosage indicator dial 422 radially about drive nut 428.

Figure 45:
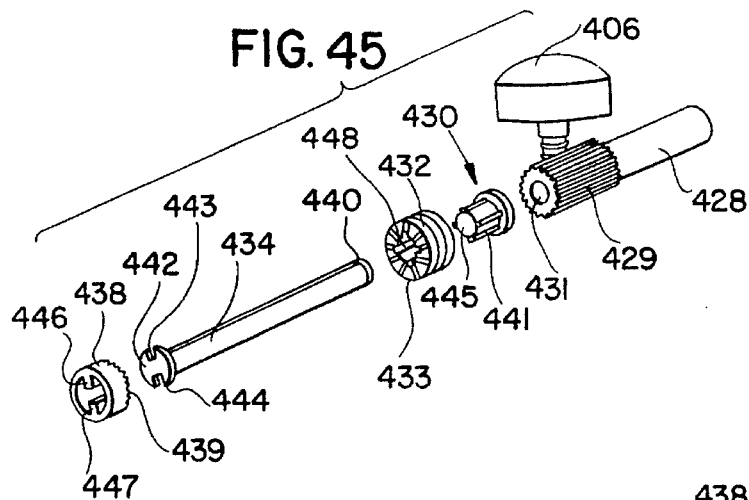
FIG. 45 is an exploded view of the metering components of the metering device of FIG. 44.
Figure 46:
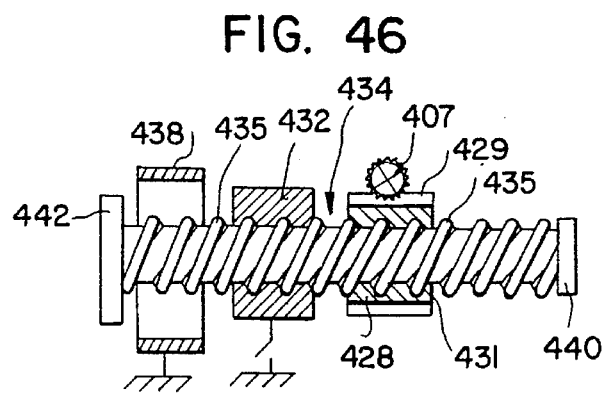
FIG. 46 is a sectional view of the components of FIG. 45.

Referring now to FIGS. 45 and 46, the components of metering mechanism 410 necessary for dosage metering are shown. Rotation of worm gear 407 meshes with and thus rotates drive nut 428 via gear 429. Drive nut 428 is internally threaded at 431 with a, for example, 28°–45° helix thread. Received within internal threads 431 is leadscrew 434 which is matingly threaded with, for example a 28°–45° helix thread 435. Radially about leadscrew 434 is brake spline 430 having mating threads 445 on the inner surface thereof and radially outwardly projecting splines 441 on the outside surface thereof. Also disposed radially about leadscrew 431 is brake clutch 432 having splines 448 on the inside surface thereof corresponding to splines 441 of brake nut 430 which is disposed radially inwardly of brake clutch 432. Leadscrew 434 has a stop .440 on one end thereof providing an insufficient dose lockout feature through contact with one end of drive nut 428. The insufficient dose lockout feature limits the metering of the dosage to a certain amount as the cartridge empties. When drive nut. 428 translates in the rearward direction drive nut 428 will contact stop 440 such that drive nut 428 cannot travel any further. This lockout feature is important since when the plunger in the cartridge is at a certain depth, the volume of insulin inside the cartridge diminishes due to the curvature of the cartridge. The metering is limited since the volume of insulin is less that the maximum metering setting. Leadscrew 434 is threaded 435, with for example a 28°–45° helix, and has on the other end a leadscrew disk 442 for contacting and urging against cartridge plunger 105 during injection. Leadscrew disk 442 includes two grooves 443, 444 which longitudinally extend the length of leadscrew 434 for constraining rotation thereof in conjunction with lugs 446, 447 of pullback nut 438 (FIG.55). When teeth 439 of pullback nut 438 are engaged, pullback nut 438 and thus leadscrew 434 cannot rotate. FIG. 46 shows that brake clutch 432 is locked against rotation during metering, but is free to rotate upon injection.

Figure 47:
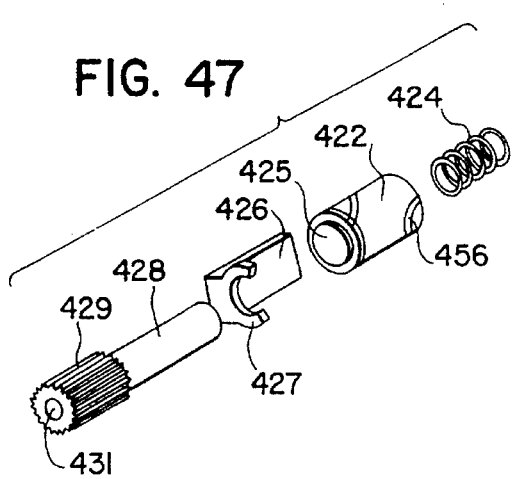
FIG. 47 is an exploded view of the injection components of the metering device of FIG. 44.
Figure 48:
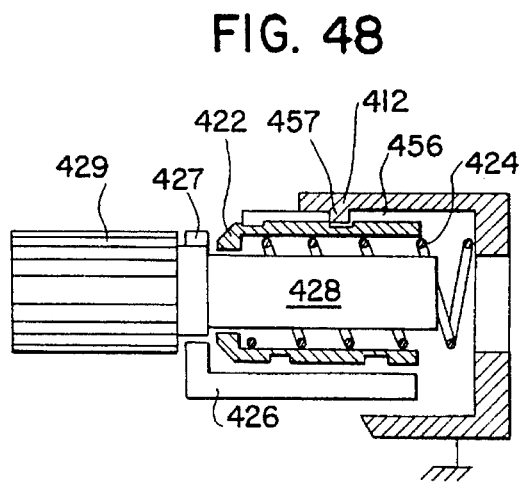
FIG. 48 is a sectional view of the components of FIG. 47.

Referring now to FIGS. 47 and 48, the dosage indication mechanism is shown. Drive nut 428 fits into collar 427 of rack 426, collar 427 transmitting torque from power assist spring 420 (FIG. 51) to drive nut 426. Dosage indicator dial 422 is barrel-shaped having an opening 425 in which drive nut 428 is received, and a cam groove or track on the outside surface thereof in which fits pin 457 of housing 402. Since pin 457 is fixed against rotation and translation, as dosage indicator 422 is translated by rearward action of drive nut 428, dosage indicator 422 also rotates thereby indicating the metered dosage in window 410 (FIG. 41). A torsion spring 424 is disposed radially inside and fastened to dosage indicator 422 and radially about drive nut 428 and fastened to housing 402. Torsion spring 424 twists as dosage indicator 422 translates rearwardly providing a bias to urge dosage indicator 422 back to its reset position when released.

Figure 49:
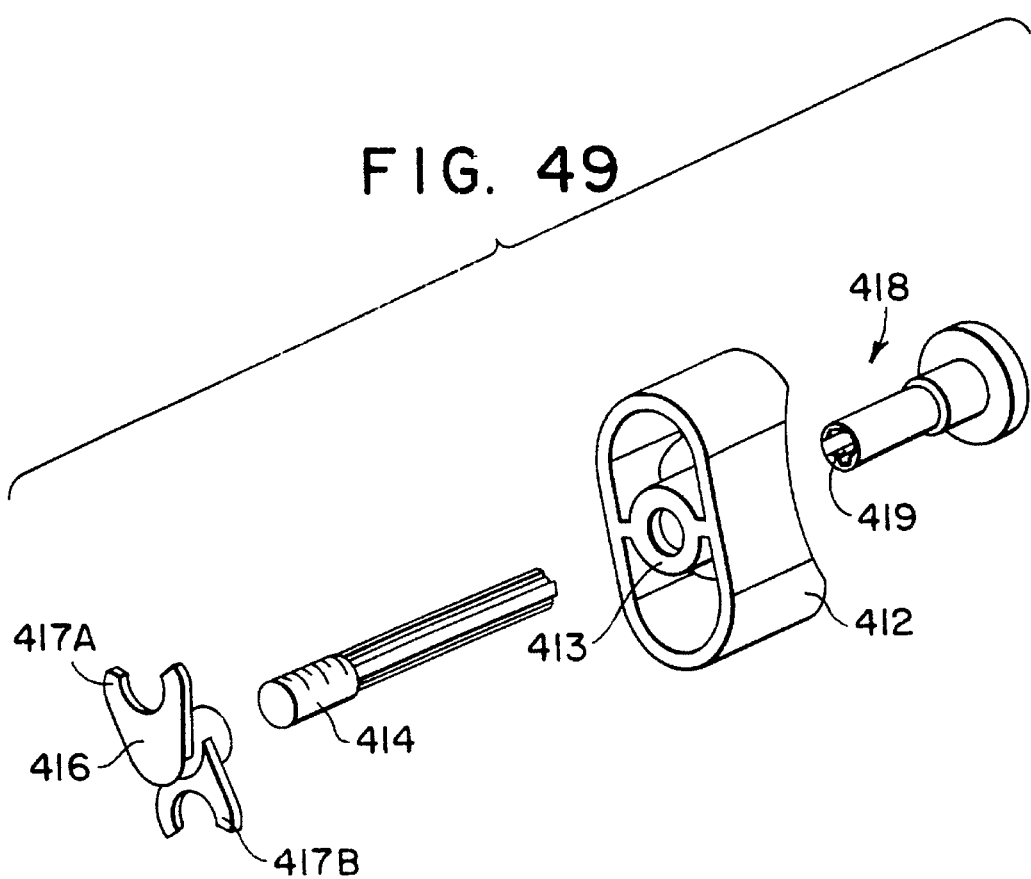
FIG. 49 is an exploded view of the plunger components of the metering device of FIG. 44.
Figure 50:
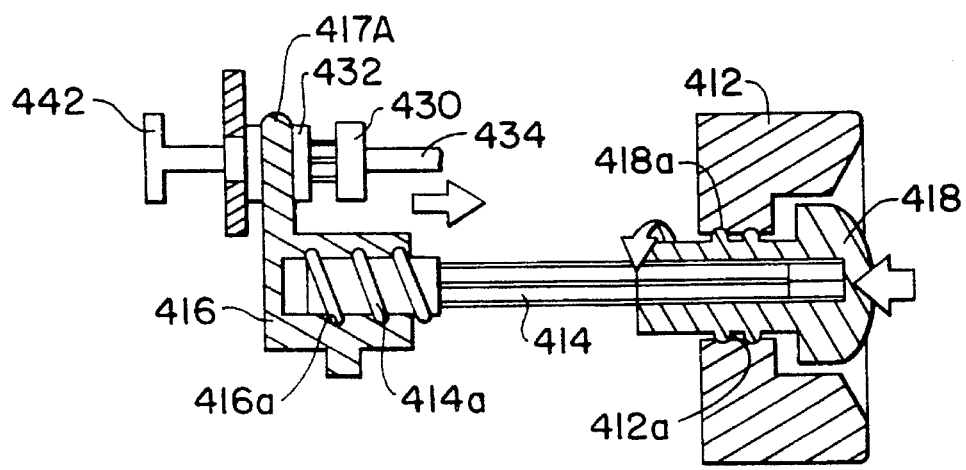
FIG. 50 is a sectional view of the components of FIG. 49.

Referring now to FIGS. 49 and 50, the brake/release mechanism components are shown. Brake trigger 418 is received in stop aperture 413 of plunger 412 such that brake trigger 4.18 protrudes slightly therefrom but has sufficient room to axially translate when pushed and reset. Brake trigger 418 is internally splined at 419 to mate with externally splined brake rod 414. Brake rod 414 also includes a high helix thread 414a on the tip distal plunger 412 mating with like high helix threads 416a on brake arm 416. Brake arm 416 includes two brake clutch actuators 417A, 417B that connect to the brake clutches 432 for axial movement thereof in response to axial movement of brake rod 414. As brake trigger 418 is depressed, high helix threads 418a and 412a rotate brake rod 414 thereby causing threads 414a and 4161 to retract brake 416.

Figure 52:
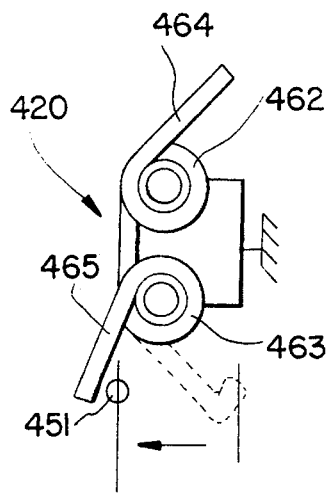
FIG. 52 is a schematic of the movement of the power assist spring.
Figure 51:
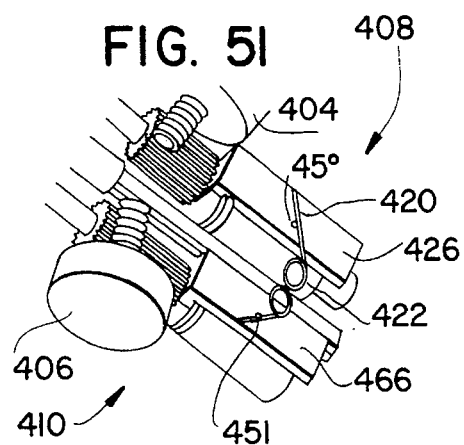
FIG. 51 is a partial view of the metering assembly of FIG. 42 showing the power assist spring.

Referring now to FIGS. 51 and 52 there is shown power assist spring 420 which is diagrammatically illustrated as being attached to a "ground" indicating that lobes 462, 463 are movably fixed to housing 402 relative to arms 464, 465. The location of power assist spring 420 is shown in FIG. 51 and extends between metering mechanisms 410 and 408, arms 464, 465 seated against pins 450, 451 of racks 426, 466. Power assist spring is preloaded, such that it tends to urge racks 426, 466 axially towards the cartridges 104, 106.

Figure 54:
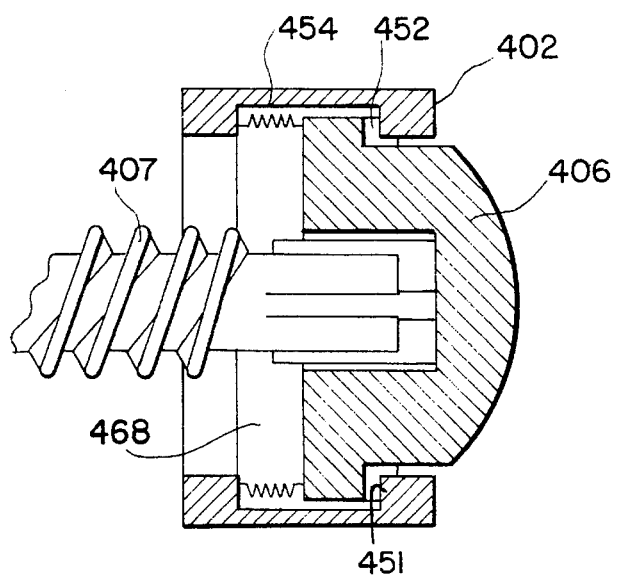
FIG. 54 is a sectional view of the metering knob assembly of the metering device of FIG. 42.
Figure 53:
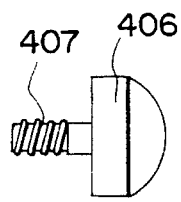
FIG. 53 is an elevational view of the metering knob of the device of FIG. 42.

Referring to FIGS. 53 and 54, the dosage knob mechanism is shown. Dosage knob 406 with worm gear 407 is seated within a cavity 468 in housing 402 and is biased by spring 454 against teeth 451 on housing 402 through ratchet 452. This provides an audible and tactile feedback for positive metering and a resolution of 36 units per revolution.

Referring now to FIG. 55, the plunger/pullback mechanism is shown. Leadscrew 434 is held against rotation by lugs 446, 447 in the mating grooves 443, 444 when pullback nut 438 is clutched to wall 460 through teeth 439 and 433. A compression spring 436 tends to urge pullback nut 438 axially away from wall 460 thereby permitting rotation of leadscrew 434. When pullback nut 438 pressed against wall 460 when cartridge 104 is loaded therein, pullback nut 438 and leadscrew 434 are locked against rotation. When cartridge 104 needs to be replaced with a new cartridge, removal of old cartridge 104 allows disengagement of pullback nut 438 from wall 460 such that leadscrew 434 and pullback nut 438 may rotate. Insertion of a new cartridge 104 rotates leadscrew 434 through a rearward translation as cartridge 104 compresses compression spring 436 to lock pullback nut 438, and thus leadscrew 434, against rotation.

The manner and form of operation of plunger-type injector 400 with all of its various components as hereinabove described with particular reference to appropriate drawings, will now be described with reference being made to FIGS. 56–59, respectively depicting the following states or stages of operation: the Ready state, the Metering state, the Injection state, and the Return state. It should be noted that the manner and form of operation of the metering mechanisms are identical, therefore only one metering mechanism will be described hereinbelow.

Referring now to FIG. 56, there is depicted an enlarged partial sectional view of injector mechanism 401. Metering mechanism 410 is shown in a Ready state wherein power assist spring 420 is preloaded to bias rack 426 (not shown) via collar 427 against drive nut 429. Leadscrew disk 442 is seated against plunger 107, prepared for metering. Torsional spring 424 biases dosage indicator sleeve 422 axially toward cartridge 106.

Referring to FIG. 57, the Metering state is depicted. Metering knob 406 is bi-directionally rotated in order to set the desired dosage amount, for example, from 1 to 50 units. As metering knob 406 is rotated, worm gear 107 meshes with spur gear 429 of drive nut 428 causing drive nut 428 to rotate about leadscrew 434. Drive nut 428 rotates about leadscrew 434 because leadscrew 434 is held from rotation by pullback nut 438 which is itself held against rotation by the clutching of teeth 439 with teeth 435 of housing wall 460. Projections 446, 447 of pullback nut 438 disposed in grooves 443, 444 of leadscrew 434 prevent rotation of leadscrew 434 as long as pullback nut 438 is engaged with the housing. Leadscrew 434 is also held against translation as drive nut 428 rotates by internally threaded brake nut 432 engaged with the splined brake spline 430, the brake nut 432 clutched against housing wall 460 through teeth 433 of brake nut 432 and teeth 435 of housing wall 460.

Thus, rotation of drive nut 428 causes rearward translation thereof along leadscrew 434. As drive nut 428 rearwardly translates rack 426, through collar 427, rack 426 further loads already pre-loaded power assist spring 420 urging drive nut 428 back to the home position. The translating drive nut pushes the dosage indicator dial 422 axially rearwardly, which also rotates to give the proper dosage indication via dosage window 410 (FIG. 41), as a pin 457 in the housing guides cam track 456 in like manner to the dosage indicator dial of injector 100. As dosage indicator dial 422 rearwardly translates, return spring 424 is twisted, urging dosage indicator dial 422, rack 426, and drive nut 428 towards cartridge 106. The desired dosage amount metered in metering mechanism 410 is translated into a travel distance of leadscrew 434 which corresponds to the travel distance of plunger 107 within cartridge 106 to inject the desired dosage. The travel distance is defined after metering between the cartridge side end of drive nut 428 and the plunger end of brake spline 430.

Once the metered amount is set, the brake release/inject state is next as depicted in FIG. 58. At this point, finger pressure on plunger 412 by the user will cause brake trigger 418 to be depressed first, which, because brake arm 416 is fixed against forward translation, creates rotation of brake rod 414. In turn, rotation of brake rod 414 via mating splines with brake trigger 418 pulls internally threaded brake arm 416 rearwardly towards brake trigger 418. Translation of brake arm 416 unseats brake clutch 432 and accompanying brake spline 430 from wall 460 with brake clutch 432 and brake spline 430 translated rearwardly. The mechanism is ready for injection.

Figure 59:
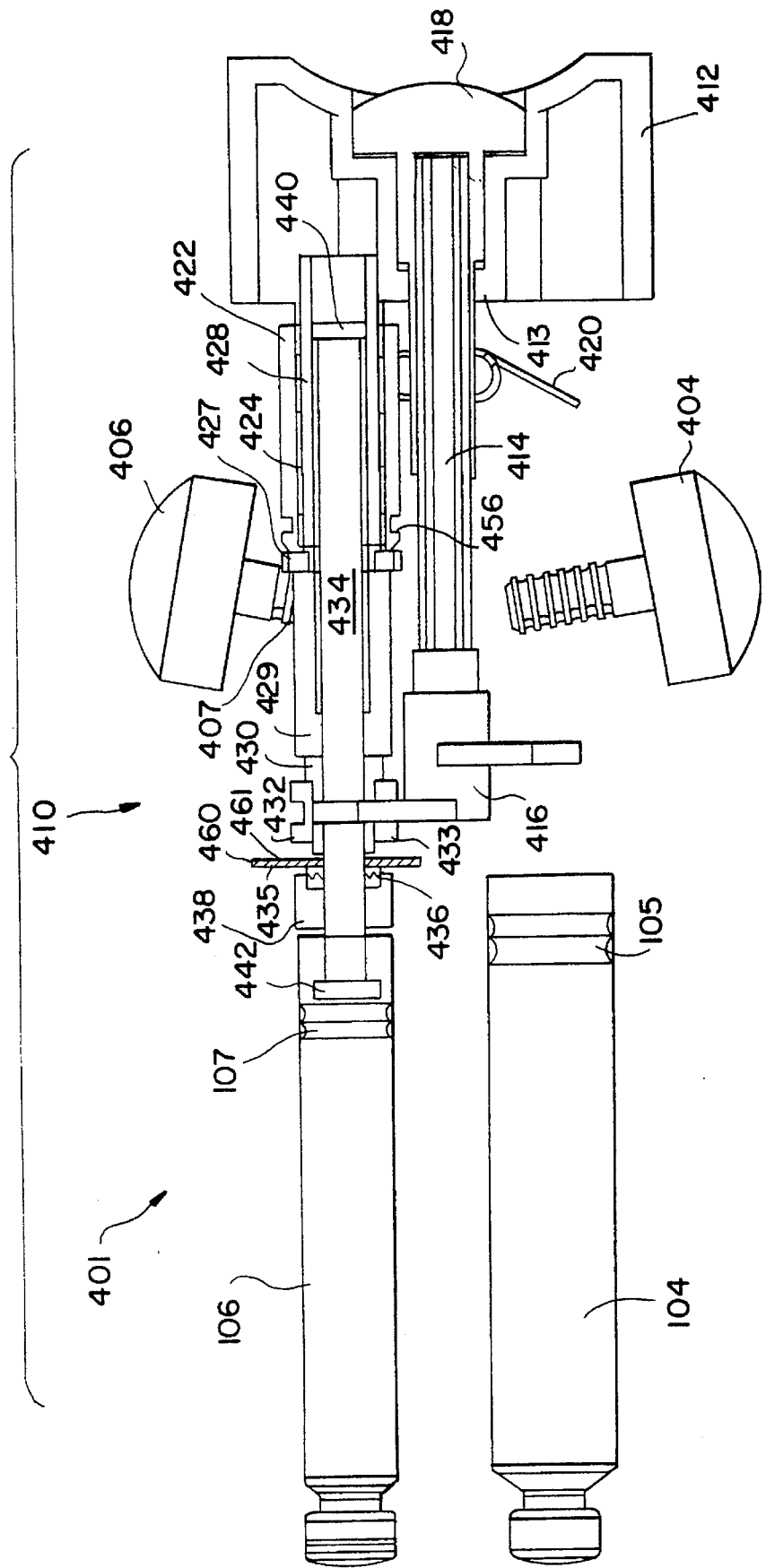
FIG. 59 is a partial sectional view of the injector device of FIG. 40 in an End of Inject state.

Referring now to FIG. 59, the brake clutch 432 is now free to rotate such that leadscrew 434 may translate, but leadscrew 434 is still restrained against rotation by pullback nut 438. Depressing plunger 412 initiates injection. As plunger 412 is depressed, power assist spring 420 assists translation of drive nut 428, rack 426, and dosage indicator dial 422 toward cartridge 106. This translates leadscrew 434 against plunger 107 to inject the liquid medication therefrom. It is important that drive nut 428 does not rotate during forward translation as this would change the dosage amount previously metered in. Mechanical friction between gear 429 and worm gear 407, along with ratchet mechanism 452 (FIG. 54) prevents drive nut 428 from rotation. Furthermore, it should be understood that the injection of liquid medication from two cartridges requires more pressure on the plunger than would a single cartridge system. Since in this embodiment, a plunger mechanism is utilized which would be depressed generally by a lone forefinger during injection, the power assist provided by power assist spring 420 provides the extra force needed to easily depress plunger via the lone forefinger and eject the liquid medication from the cartridges.

Constant force on plunger 412 by the user with the aid of power assist spring 420 completes the injection. Dosage indicator dial 422 rotates and translates back to a zero dosage position by the bias exerted thereagainst by return spring 424, with dosage indicator dial 422 guided by pin 457 in cam track 456. The unit is now at the end of the Inject state and again in the Ready state.

Leadscrew 434 remains in the forward translated position such that further advancement during injection will translate the cartridge plunger. Drive nut 428 forwardly translates, stopping in the Ready state.

In summary, plunger-type injector 400 is a hand-held injector. Once the dosage amount is metered in as described hereinabove, the plunger mechanism is depressed by the user generally with a lone forefinger. In depressing the plunger, the brake trigger is likewise depressed releasing the brake clutch, which in one continuing motion, allows the injection of the medications with the aid of the power assist spring. The brake clutch holding the leadscrew prevents drooling of the medication from the needle caused by pressure exerted against the plunger before actual injection.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A medication dispensing device for effecting the simultaneous delivery of two injectable products, comprising:
   a housing;
   a first cartridge received in said housing for containing and sealing a first injectable product therein, said first cartridge having a first exit end and including a first plunger therein;
   a second cartridge received in said housing for containing and sealing a second injectable product therein, said second cartridge having a second exit end and including a second plunger therein;
   a first dosage metering mechanism disposed in said housing and including a first dosage adjuster coupled to a first plunger-engageable member such that upon adjustment of said first dosage adjuster, said first member is axially advanceable a first distance with respect to said housing to establish a first set dosage of injectable product to be delivered without effecting delivery of the first injectable product;
   a second dosage metering mechanism disposed in said housing and including a second dosage adjuster coupled to a second plunger-engageable member such that upon adjustment of said second dosage adjuster, said second member is axially advanceable a second distance with respect to said housing to establish a second set dosage of injectable product to be delivered without effecting delivery of the second injectable product;
   a manifold secured to said first and second exit ends of said first and second cartridges, respectively, for enabling the mixing of said first and second set dosages of said first and second injectable products upon delivery from said respective cartridges into said manifold, said manifold being in fluid communication with said first and second cartridges and containing a common exit for enabling the mixed injectable product to be delivered to a user; and
   an injector mechanism coupled to said first and second members for simultaneously axially advancing said first and second members a distance sufficient to engage and axially advance said first and second plungers, respectively, to effect simultaneous delivery of said first and second set dosages into said manifold and out through said cannula.

2. The apparatus of claim 1, wherein said injector mechanism includes a carrier, wherein said first and second members are secured to said carrier and axially movable therewith, said carrier being axially advanceable upon actuation of said injector mechanism to simultaneously advance said members to effect simultaneous delivery of said first and second set dosages.

3. The apparatus of claim 1, wherein the axial advancement of said first and second plungers in said first and second cartridges, respectively, defines a first axis of delivery and a second axis of delivery, respectively, said first and second axes of delivery being generally parallel to one another, wherein said injector mechanism includes a hand-operated actuator movable in a direction transverse to said axes of delivery to effect delivery of the mixed injectable product.

4. The apparatus of claim 1, wherein the axial advancement of said first and second plungers in said first and second cartridges, respectively, defines a first axis of delivery and a second axis of delivery, respectively, said first and second axes of delivery being generally parallel to one another, wherein said injector mechanism includes a hand-operated actuator movable in a direction generally parallel to said axes of delivery to effect delivery of the mixed injectable product.

5. The apparatus of claim 4, wherein a power assist spring is secured to said housing and coupled to said first and second members said spring being preloaded to urge said first and second members axially toward said first and second cartridges, respectively, upon actuation of said injection mechanism, wherein said power assist spring aids the user in completion of the injection.

6. The apparatus of claim 1, wherein said injector mechanism operates independently of said first and second metering mechanisms.

7. The apparatus of claim 1, wherein said first and second dosage adjustors are rotatable to effect advancement of said first and second members.

8. The apparatus of claim 7, wherein said first and second dosage adjusters are rotatable in both a clockwise direction and a counterclockwise direction thereby enabling each of said respective first and second members to be translated axially forwardly and rearwardly to enable a user to selectively increase and decrease said first and second set dosages prior to actuating said injector mechanism.

9. The apparatus of claim 1, wherein said first and second members are leadscrews coupled to said respective first and second dosage metering mechanisms in such a manner that adjustment of each said respective dosage adjustor causes said respective leadscrew to translate axially in a non-rotary manner within said housing.

10. An apparatus for effecting delivery of an injectable product, comprising:
    a housing;
    a cartridge received in said housing for containing and sealing an injectable product therein, said cartridge including an exit end and a plunger axially movable in said cartridge to define an axis of ejection of the injectable product from said cartridge;
    a manually adjustable dosage metering mechanism disposed in said housing for enabling a user to selectively set a dosage of the injectable product to be delivered without effecting delivery of the injectable product from said cartridge; and a delivery mechanism including an elongate member for engaging and axially advancing said plunger a distance sufficient to cause said set dosage to be delivered out of said cartridge, said delivery mechanism including a hand operated actuator movable in a direction transverse to the axis of ejection, wherein each incremental movement of said actuator causes a corresponding incremental movement of said elongate member, wherein a predetermined movement of said actuator in said transverse direction causes delivery of said set dosage.

11. The apparatus of claim 10, wherein said dosage metering mechanism includes a dosage adjustor coupled to a leadscrew such that upon rotation of said dosage adjustor, said leadscrew is axially advanceable a given distance with respect to said housing to establish said set dosage of injectable product to be delivered without effecting delivery of the injectable product.

12. A medication dispensing device for effecting the simultaneous delivery of two injectable products through a single cannula, comprising:

a housing;

a first cartridge received in said housing for containing and sealing a first injectable product therein, said first cartridge having a first exit end and including a first plunger therein;

a second cartridge received in said housing for containing and sealing a second injectable product therein, and said second cartridge having a second exit end and including a second plunger therein;

a dosage metering mechanism disposed in said housing to establish a first set dosage of the first injectable product to be delivered, and a second set dosage of the second injectable product to be delivered;

an injector mechanism to engage and axially advance said first and second plungers to effect simultaneous delivery of said first and second set dosages out of said first and second cartridges, respectively; and a manifold secured to said first and second exit ends of said first and second cartridges, respectively, for enabling the mixing of said first and second set dosages of said first and second injectable products upon delivery from said respective cartridges into said manifold, said manifold comprising a front housing, a rear housing including a first cannula extending into said first cartridge and a second cannula extending into said second cartridge, and a rubber septum disposed between said front and rear housings, said septum comprising a substantially flat surface adjacent ends of said first and second cannulas, said front housing including a delivery needle therein for delivery of injectable product through said delivery needle, wherein a first fluid path for the first injectable product is formed in said manifold from said first cannula to said delivery needle and a second fluid path for the second injectable product is formed in said manifold from said second cannula to said delivery needle, wherein a first flat portion of a first surface of said septum is in fluid-tight engagement with a first flat sealing surface of said rear housing to define a first pressure-actuated valve portion in said first fluid path and wherein a second flat portion of a second surface of said septum is in fluid-tight engagement with a second flat sealing surface of said rear housing to define a second pressure-actuated valve portion in said second fluid path, said first and second valve portions being biased in a closed position to prevent the flow of injectable product therethrough, said first and second valve portions being flexible enough to open to permit the flow therethrough of the first and second injectable products, respectively, upon the expulsion of the first and second injectable products out of said first and second cannulas, respectively.

13. The device of claim 12, wherein said front housing includes an elongate recessed portion formed therein to define a channel, said channel being part of said first and second fluid paths and in engagement with said first and second valve portions of said septum.

14. The device of claim 12, wherein said septum includes a first opening extending therethrough in communication with said first flow path, a second opening extending therethrough in communication with said second flow path and a third opening extending therethrough, said third opening receiving said delivery needle.

15. An apparatus for the delivery of an injectable product, comprising:

a housing;

a container mounted within said housing and including a plunger, an exit and an injectable product between said plunger and said exit;

a drive stem disposed in said housing and drivingly coupled to said plunger;

a drive assembly mounted to said housing and axially movable in said housing between a dose-setting position and an injection position for moving said drive stem to drive said plunger within said container, said drive assembly including a first ratchet element; and a dose setting assembly coupled to said drive assembly to establish a set dosage of injectable product to be delivered, said dose setting assembly including an indicator element being movable from a zero dose reference position against a biasing force to a specific dose reference position upon the setting of a desired dose to be delivered, said dose setting assembly including a mechanism in engagement with said indicator element to maintain said indicator element in said specific dose position while said drive assembly is in said dose-setting position, said mechanism being movable out of engagement with said indicator element upon movement of said drive assembly from said dose-setting position to said injection position, thereby enabling said indicator element to be automatically biased back to its zero dose reference position.

16. An apparatus for the delivery of an injectable product, comprising:

a housing;

a container mounted within said housing and including a plunger, an exit and an injectable product between said plunger and said exit;

a drive stem disposed in said housing and drivingly coupled to said plunger;

a drive assembly mounted to said housing and axially movable in said housing between a dose-setting position and an injection position for moving said drive stem to drive said plunger within said container, said drive assembly including a first element; and a dose setting assembly coupled to said drive assembly to establish a set dosage of injectable product to be delivered, said dose setting assembly comprising a rotatable element including a dose setting knob and a second element, said drive assembly being positioned such that said first element is in locking engagement with said second element while said drive assembly is in said dose-setting position, and said first element is moved into unlocked relationship with said second element upon movement of said drive assembly from said dose-setting position to said injection position;

while said drive assembly is in said dose-setting position, said rotatable element is rotatable from a predetermined initial radial position against the bias of a spring to a selective final radial position for selectively setting the dosage of injectable product to be delivered, wherein said rotatable element is biased back to said initial radial position upon movement of said drive assembly from said dose-setting position to said injection position due to the disengagement of said first member from said second member.

17. An apparatus for the delivery of an injectable product, comprising:

a housing;

a container mounted to said housing and including a plunger, an exit and an injectable product between said plunger and said exit;

a drive stem disposed in said housing and drivingly coupled to said plunger;

a drive assembly mounted to said housing and axially movable in said housing between a pre-injection position and a post-injection position for moving said drive stem to drive said plunger within said container, said drive assembly including a first ratchet element, and a tubular element coupled to said drive stem such that said tubular element is rotatable with respect to said drive stem, wherein relative rotation between said tubular element and said drive stem controls the amount of telescopic extension of said drive stem from said tubular element to establish a set dosage of injectable product to be delivered, said drive stem being axially movable with said tubular element between said pre-injection position and said post-injection position; and a dose setting assembly coupled to said drive assembly and comprising a rotatable element having an end in the form of a dose setting knob and a second ratchet element engageable with said first ratchet element while said drive assembly is in said pre-injection position, wherein said dose setting knob is coupled to said tubular element while said drive assembly is in said pre-injection position so that rotation of said knob with respect to said housing results in rotation of said tubular element, said rotatable element being rotatable against the force of a spring from an initial radial position to a selective final radial position for selectively advancing said drive stem to set the dosage of injectable product to be delivered, said first ratchet element being spaced from said second ratchet element while said drive assembly is in said post-injection position, whereby said spring biases said rotatable element from said final radial position to said initial radial position upon movement of said drive assembly from said pre-injection position to said post-injection position.

18. The apparatus of claim 17, wherein said plunger is axially movable in said container toward said exit to define an axis of ejection of said injectable product, wherein said drive assembly includes an actuator movable in a direction transverse to said axis of ejection for moving said drive assembly between said pre-injection position to said post-injection position.

19. The apparatus of claim 17, wherein said rotatable member includes a plurality of numerals spaced about said rotatable member, wherein said housing includes an opening therein and said rotatable member is arranged in said housing such that a numeral appears in said opening, thereby indicating to the user the number of dosage units constituting said set dosage.

20. The apparatus of claim 19, wherein the numeral 0 appears in said opening while said rotatable member is in its initial radial position.

21. An apparatus for the delivery of an injectable product, comprising:

a housing;

a container mounted to said housing and including a plunger, an exit and an injectable product between said plunger and said exit;

plunger-engagement means disposed in said housing for drivingly engaging said plunger;

drive means mounted to said housing for moving said plunger-engagement means between a pre-injection position and a post-injection position to drive said plunger within said container, said drive means including a first element, and a nut means coupled to said plunger-engagement means for rotation with respect to said plunger-engagement means, wherein relative rotation between said nut means and said plunger-engagement means controls the amount of telescopic extension of said plunger-engagement means from said nut means to establish a set dosage of injectable product to be delivered, said plunger-engagement means being axially movable with said nut means between said pre-injection position and said post-injection position; and dose setting means for setting a dosage of injectable product to be delivered, said dose setting means coupled to said drive means and comprising a rotatable element including a dose setting knob and a second element engageable with said first element while said drive means is in said pre-injection position, wherein said dose setting knob is coupled to said nut means while said plunger-engagement means is in said pre-injection position so that rotation of said knob with respect to said housing results in rotation of said nut means, said rotatable element being rotatable against the force of spring means from an initial radial position to a selective final radial position for selectively advancing said plunger-engagement means to set the dosage of injectable product to be delivered, said first ratchet element being spaced from said second ratchet member while said plunger-engagement means is in said post-injection position, whereby said spring means biases said rotatable element from said final radial position to said initial radial position upon movement of said plunger-engagement means from said pre-injection position to said post-injection position.

22. The apparatus of claim 21, wherein said plunger is axially movable in said container toward said exit to define an axis of ejection of said injectable product, wherein said drive means includes an actuator movable in a direction transverse to said axis of ejection for moving said plunger-engagement means between said pre-injection position to said post-injection position.

23. The apparatus of claim 21, wherein said rotatable member includes a plurality of numerals spaced about said rotatable member, wherein said housing includes an opening therein and said rotatable member is arranged in said housing such that a numeral appears in said opening, thereby indicating to the user the number of dosage units constituting said set dosage.

24. The apparatus of claim 23, wherein the numeral 0 appears in said opening while said rotatable member is in its initial radial position.

25. An apparatus for the delivery of an injectable product, comprising:

a housing;

a container received in said housing and including a plunger, an exit and an injectable product between said plunger and said exit;

a drive stem disposed in said housing and drivingly coupled to said plunger; and a drive assembly mounted to said housing and axially movable in said housing for moving said drive stem to drive said plunger within said container;

wherein a locking mechanism is engageable with said drive stem and configured to restrict rotation of said drive stem with respect to said housing, said locking mechanism being in engagement with said drive stem while said container is securely mounted in said housing to prevent rotation of said drive stem with respect to said housing, said locking mechanism being automatically disengaged from said drive stem upon removal of said container from said housing, thereby permitting said drive stem to be rotated with respect to said housing.

26. An apparatus for the delivery of an injectable product, comprising:

a housing having a proximal end and a distal end;

a container received in said distal end of said housing and including a plunger, an exit and an injectable product between said plunger and said exit;

a drive stem disposed in said housing and drivingly coupled to said plunger;

a dosage metering mechanism disposed in said housing to establish a first set dosage of the first injectable product to be delivered; and a drive assembly mounted to said housing and axially movable in said housing for reciprocatingly moving said drive stem to drive said plunger within said container, wherein a locking mechanism is engagable with said drive stem and configured to prevent axial movement of said drive stem toward said proximal end of said housing independent of said dosage metering mechanism and said drive assembly, said locking mechanism being in engagement with said drive stem while said container is securely mounted in said housing to prevent said independent axial movement of said drive stem with respect to said housing, said locking mechanism being automatically disengaged from said drive stem upon removal of said container from said housing, thereby permitting said drive stem to be axially moved toward the proximal end of said housing independent of said dosage metering mechanism and drive assembly.

27. An apparatus for the delivery of an injectable product, comprising:

a housing;

a container received in said housing and including a plunger, an exit and an injectable product between said plunger and said exit;

a drive stem disposed in said housing and drivingly coupled to said plunger; and a drive assembly mounted to said housing and axially movable in said housing for moving said drive stem to drive said plunger within said container, wherein a rotatable piece is secured to said drive stem for rotation therewith, and a locking sleeve is disposed about said drive stem and configured to restrict rotation of said rotatable piece with respect to said housing, said rotatable piece and said locking sleeve being biased in unlocked relationship with one another, said rotatable piece and said locking sleeve being forced into locked engagement with one another while said container is mounted to said housing to prevent rotation of said rotatable piece and said drive stem with respect to said housing, said rotatable piece and said locking sleeve being automatically disengaged from one another upon removal of said container from said housing, thereby permitting said rotatable piece and said drive stem to be rotated with respect to said housing.

28. The apparatus of claim 27, wherein a spring is positioned in said housing with respect to said rotatable piece and said locking means to apply a biasing force sufficient to separate a first locking element of said rotatable piece from a second locking element of said locking means, said spring means being positioned in said housing such that upon said container being secured to said housing end, said spring means is compressed sufficiently to permit said rotatable piece to lockingly engage with said locking means.

29. The apparatus of claim 27, wherein said rotatable piece includes a first set of ratchet teeth and said locking means includes a second set of ratchet teeth, wherein said first set of ratchet teeth are in engagement with said second set of ratchet teeth while said container is mounted to said housing.

30. The apparatus of claim 27, wherein said plunger-engagement means is moveable axially from said housing end and toward a second and opposite housing end upon said container being removed from said housing.

31. An apparatus for the delivery of an injectable product, comprising:

a housing;

a container received in said housing and including a plunger, an exit and an injectable product between said plunger and said exit;

plunger-engagement means disposed in said housing for drivingly engaging said plunger; and drive means mounted to said housing and axially movable in said housing for moving said plunger-engagement means to drive said plunger within said container, wherein a rotatable piece is secured to said drive stem for rotation therewith, and a locking means is disposed about said drive stem and configured to restrict rotation of said rotatable piece with respect to said housing, said rotatable piece and said locking means being in unlocked relationship with one another, said rotatable piece and said locking means being forced into locked engagement with one another while said container is mounted to said housing to prevent rotation of said rotatable piece and said plunger-engagement means with respect to said housing, said rotatable piece and said locking means being automatically disengaged from one another upon removal of said container from said housing, thereby permitting said rotatable piece and said plunger-engagement means to be rotated with respect to said housing.

32. An apparatus for effecting delivery of an injectable product, comprising:
- a first cartridge for containing and sealing a first injectable product therein, said first cartridge having a first exit end and including a first plunger axially movable in said first cartridge to define a first axis of ejection of the first injectable product from said first cartridge;
- a second cartridge for containing and sealing a second injectable product therein, said second cartridge having a second exit end and including a second plunger axially movable in said second cartridge to define a second axis of ejection of the second injectable product from said second cartridge;
- a housing having a proximal end and a distal end, wherein said first and second cartridges are mounted to said distal end;
- a manually operable dosage metering mechanism disposed in said housing for enabling a user to selectively set a dosage of at least one of the first and second injectable products to be delivered without effecting delivery of the respective injectable product from said respective cartridge;
- a delivery mechanism for simultaneously axially advancing said first and second plungers a distance sufficient to effect simultaneous delivery of said first and second set dosages out of said respective cartridges, said delivery mechanism including an actuator movable in a direction transverse to said axes of delivery, wherein movement of said actuator in said transverse direction causes delivery of said first and second set dosages; and
- a manifold secured to said first and second exit ends of said cartridges for enabling the mixing of said set dosages of said first and second injectable products and the delivery of a mixed injectable product upon movement of said actuator, said manifold including a cannula extending into each of said cartridges and a common exit in fluid communication with said cartridges for enabling the mixed injectable product to be delivered to a user.

33. The apparatus of claim 32, wherein said first and second members are secured to a carrier and are axially moveable with said carrier, said carrier being axially advanceable upon actuation of said actuator to simultaneously axially advance said members to engage and axially advance said respective plungers in said cartridges to effect simultaneous delivery of said set dosages.

34. The apparatus of claim 32, wherein said actuator includes a side plate, wherein said side plate is coupled to a driving pin associated with each said member such that upon actuation of said actuator, said side plate and pin are moved axially forwarding thus causing said members to be moved axially forwardly to engage and axially advance said respective plungers.

35. A method of delivering a selected dosage of injectable product, the method comprising the steps of:
- rotating a knob extending from an injector housing to set a dosage of injectable product to be delivered out of a container mounted to an end of the housing, wherein the injectable product is in the container between a plunger and an exit end of the container, wherein movement of the plunger toward the exit end defines an axis of ejection of the injectable product from the container; and
- continuously moving an actuator in a direction transverse to the axis of ejection to move the plunger and effect delivery of the injectable product.

36. The method of claim 35, wherein the step of continuously moving the actuator includes moving the actuator through a given angular range of motion, wherein incremental movement of the actuator results in a corresponding incremental axial advancement of a drive assembly which carries a plunger-engaging stem.

37. The method of claim 35, wherein the step of rotating includes rotating the knob in a first rotational direction to increase the set dosage and then in a second and opposite rotational direction in order to decrease the set dosage.

38. The method of claim 35, wherein movement of the actuator causes the knob to be rotated back to an initial rotational position.

39. A method of delivering a selected dosage of mixed injectable product, the method comprising the steps of:
- rotating a first knob of a first dosage metering mechanism disposed in an injector housing to set a first set dosage of first injectable product to be delivered out of a first container mounted in the housing, wherein the first injectable product is in the first container between a first plunger and a first exit end of the first container, wherein the first plunger is movable toward the first exit end along a first axis of ejection of the first injectable product from the first container;
- rotating a second knob of a second dosage metering mechanism disposed in the injector housing to set a second set dosage of second injectable product to be delivered out of a second container mounted in the housing, wherein the second injectable product is in the second container between a second plunger and a second exit end of the second container, wherein the second plunger is movable toward the second exit end along a second axis of ejection of the second injectable product from the second container, the second axis being generally parallel to the first axis; and
- moving an actuator in a direction transverse to the first and second axes of ejection to simultaneously axially advance first and second plunger-engagement members in the housing to axially advance the first and second plungers, respectively, to effect simultaneous delivery of the first and second set dosages into a manifold attached to the first and second exit ends of the first and second containers and out through a needle extending from the manifold.

40. The method of claim 39, wherein the step of moving the actuator includes moving the actuator through a given angular range of motion, wherein incremental movement of the actuator results in a corresponding incremental axial advancement of a drive assembly which carries the first and second members.

41. The method of claim 39, wherein the step of rotating includes rotating at least one of the first and second knobs in a first rotational direction to increase the respective set dosage and then in a second and opposite rotational direction in order to decrease the respective set dosage.

42. The method of claim 39, wherein movement of the actuator causes at least one of the first and second knobs to be rotated back to an initial rotational position.

43. A method of delivering a selected dosage of injectable product, wherein the injectable product is in the container between a plunger and an exit end of the container, wherein movement of the plunger toward the exit end defines an axis of ejection of the injectable product from the container, the method comprising the steps of:
- moving a wing mechanism through a given angular range of motion from a first angular position to a second angular position, wherein movement of the wing is in a direction transverse to the axis of ejection;

rotating a knob of a dosage metering mechanism disposed in an injector housing to set a dosage of injectable product to be delivered out of the container mounted to an end of the housing; and after rotation of the knob, moving the wing mechanism from the second position to the first position to effect delivery of the injectable product.

44. The method of claim 43, wherein the step of rotating includes rotating the knob in a first rotational direction to increase the set dosage and then in a second and opposite rotational direction in order to decrease the set dosage.

45. The method of claim 43, wherein movement of the wing mechanism from the second position to the first position causes the knob to be rotated back to an initial rotational position.

46. The method of claim 43, including the step of removing the container from the housing while the wing mechanism is in the first position.

47. The method of claim 46, including the step of attaching a second container to the housing.

48. The method of claim 47, wherein the step of attaching the second container to the housing includes the steps of causing the plunger to engage a plunger-engagement member in the injector housing, forcing the plunger-engagement member to translate axially within the housing toward the knob, and securing the second container within the housing.

49. A method of delivering a selected dosage of injectable product, the method comprising the steps of:

rotating a knob of a dosage metering mechanism disposed in an injector housing to set a dosage of injectable product to be delivered out of a container mounted to an end of the housing;

applying a force to an actuator to simultaneously axially advance a plunger-engagement stem to engage and axially advance a plunger to effect delivery of the set dosage from the container; and causing a supplemental force to be applied to the plunger-engagement stem upon application of the force to the actuator, wherein the supplemental force aids in the axial advancement of the plunger-engagement stem.

50. A method of delivering a selected dosage of two injectable products, the method comprising the steps of:

rotating a first knob of a first dosage metering mechanism disposed in an injector housing to set a first set dosage of first injectable product to be delivered out of a first container mounted to an end of the housing;

rotating a second knob of a second dosage metering mechanism disposed in the injector housing to set a second dosage of a second injectable product to be delivered out of a second container mounted to the end of the housing;

applying a force to an actuator to simultaneously axially advance first and second plunger-engagement stems to engage and axially advance first and second plungers to effect simultaneous delivery of the first and second set dosages from the first and second containers, respectively; and causing a supplemental force to be applied to the first and second plunger-engagement stems upon application of the force to the actuator, wherein the supplemental force aids in the axial advancement of the first and second plunger-engagement stems.

51. A method of delivering a selected dosage of injectable product, the method comprising the steps of:

attaching a variable volume container of injectable product to a housing, thereby causing a plunger-engagement stem within the housing to become locked against rotation with respect to the housing;

setting a dosage of injectable product to be delivered out of the container;

moving an actuator to effect nonrotating axial advancement of the plunger-engagement stem to effect delivery of the set dosage of injectable product out of an exit end of the container;

removing the container from the housing thereby automatically enabling the plunger-engaging stem to rotate with respect to the housing; and causing the plunger-engaging stem to rotate with respect to the housing and simultaneously axially move toward an opposite end of the housing.

52. The method of claim 51, including the step of attaching a second container to the housing, thereby automatically causing the plunger-engaging stem to axially move toward the opposite end of the housing and then become locked against rotation with respect to the housing.

53. A medication dispensing device for effecting the simultaneous delivery of two injectable products, comprising:

a housing;

a first cartridge received in said housing for containing and sealing a first injectable product therein, said first cartridge having a first exit end and including a first plunger therein;

a second cartridge received in said housing for containing and sealing a second injectable product therein, said second cartridge having a second exit end and including a second plunger therein;

means disposed in said housing for enabling a user to establish a first set dosage of said first injectable product and a second set dosage of said second injectable product to be delivered without effecting delivery of the first and second injectable products, respectively;

a manifold secured to said first and second exit ends of said first and second cartridges, respectively, for enabling the mixing of said first and second set dosages of said first and second injectable products upon delivery from said respective cartridges into said manifold, said manifold being in fluid communication with said first and second cartridges and containing a common exit for enabling the mixed injectable product to be delivered to a user; and an injector mechanism coupled to said first and second cartridges for simultaneously axially advancing said first and second plungers to effect simultaneous delivery of said first and second set dosages into said manifold and out through said cannula.

54. An apparatus for effecting delivery of an injectable product, comprising:

a housing;

a cartridge received in said housing for containing and sealing an injectable product therein, said cartridge including an exit end and a plunger axially movable in said cartridge to define an axis of ejection of the injectable product from said cartridge;

means disposed said housing for enabling a user to selectively set a dosage of the injectable product to be delivered without effecting delivery of the injectable product from said cartridge; and a delivery mechanism including an elongate member for engaging and axially advancing said plunger a distance sufficient to cause said set dosage to be delivered out of said cartridge, said delivery mechanism including a hand operated actuator movable in a direction transverse to the axis of ejection, wherein of said actuator in said transverse direction causes delivery of said set dosage.

55. A method of delivering a selected dosage of mixed injectable product, the method comprising the steps of:

actuating a dosage metering mechanism disposed in an injector housing to set a set dosage of injectable product to be delivered out of a container mounted to the housing, wherein the injectable product is in the container between a plunger and an exit end of the container, wherein movement of the plunger toward the exit end defines an axis of ejection of the injectable product from the container; and moving an actuator in a direction transverse to the axis of ejection to axially advance the first member to axially advance the first plunger to effect delivery of the set dosage out through a needle extending from the exit end.

* * * * *